(12) United States Patent
Artaki et al.

(10) Patent No.: US 11,602,379 B2
(45) Date of Patent: Mar. 14, 2023

(54) ORTHOPEDIC DEROTATION DEVICES AND METHODS OF INSTALLATION THEREOF

(71) Applicant: GLOBUS MEDICAL, INC., Audubon, PA (US)

(72) Inventors: Alexander Artaki, Philadelphia, PA (US); Khiem Pham, Chalfont, PA (US); Doug Cahill, Lititz, PA (US); Stephan Lawson, Upper Darby, PA (US); Michael Zweizig, Fleetwood, PA (US); David Leff, Philadelphia, PA (US); Aditya Ingalhalikar, Pune (IN)

(73) Assignee: Globus Medical, Inc., Audubon, PA (US)

(*) Notice: Subject to any disclaimer, the term of this patent is extended or adjusted under 35 U.S.C. 154(b) by 0 days.

(21) Appl. No.: 16/871,362

(22) Filed: May 11, 2020

(65) Prior Publication Data

US 2021/0346063 A1 Nov. 11, 2021
US 2022/0401132 A9 Dec. 22, 2022

Related U.S. Application Data

(63) Continuation of application No. 16/015,770, filed on Jun. 22, 2018, now Pat. No. 10,687,867, which is a continuation of application No. 15/598,572, filed on May 18, 2017, now Pat. No. 10,028,771, which is a continuation of application No. 14/665,273, filed on Mar. 23, 2015, now Pat. No. 9,681,899.

(51) Int. Cl.
*A61B 17/70* (2006.01)

(52) U.S. Cl.
CPC ........ *A61B 17/7047* (2013.01); *A61B 17/708* (2013.01)

(58) Field of Classification Search
CPC .......................................... A61B 17/7076–708
See application file for complete search history.

(56) References Cited

U.S. PATENT DOCUMENTS

| | | |
|---|---|---|
| 5,984,865 A | 11/1999 | Farley et al. |
| 6,083,225 A | 7/2000 | Winslow |
| D462,245 S | 9/2002 | Friedman et al. |
| 7,794,464 B2 | 9/2010 | Bridwell |
| 7,951,168 B2 | 5/2011 | Chao et al. |
| 7,951,175 B2 | 5/2011 | Chao |
| 8,007,516 B2 | 8/2011 | Chao |
| 8,038,699 B2 | 10/2011 | Cohen |
| 8,043,343 B2 | 10/2011 | Miller et al. |
| 8,123,751 B2 | 2/2012 | Shluzas |
| 8,162,952 B2 | 4/2012 | Cohen |
| 8,221,474 B2 | 7/2012 | Bridwell |
| 8,277,453 B2 | 10/2012 | Kave |
| 8,353,826 B2 | 1/2013 | Weiman |

(Continued)

FOREIGN PATENT DOCUMENTS

| | | |
|---|---|---|
| EP | 2353530 A1 | 8/2011 |
| JP | 2010527650 A | 8/2010 |

(Continued)

*Primary Examiner* — Nicholas J Plionis

(57) ABSTRACT

Embodiments herein are generally directed to derotation systems, apparatuses, and components thereof that can be used in spinal derotation procedures, as well as methods of installation. The derotation systems may include a plurality of derotation towers and clamp members.

13 Claims, 9 Drawing Sheets

(56) References Cited

U.S. PATENT DOCUMENTS

| | | |
|---|---|---|
| 8,465,529 B2 | 6/2013 | Choi |
| 8,472,944 B2 | 6/2013 | Shah |
| 8,491,588 B2 | 7/2013 | Wall |
| 8,512,343 B2 | 8/2013 | Dziedzic |
| 8,540,718 B2 | 9/2013 | Dauster |
| 8,551,141 B2 | 10/2013 | Gephart |
| 8,603,094 B2 | 12/2013 | Walker |
| 8,608,746 B2 | 12/2013 | Kolb |
| 8,679,128 B2 | 3/2014 | Seelig |
| 8,709,044 B2 | 4/2014 | Chao |
| 8,764,756 B2 | 7/2014 | Jones |
| 8,845,640 B2 | 9/2014 | McLean |
| 8,986,349 B1 * | 3/2015 | German ............ A61B 17/7068 606/279 |
| 2006/0200132 A1 * | 9/2006 | Chao ................ A61B 17/7077 606/86 A |
| 2007/0213596 A1 | 9/2007 | Hamada |
| 2008/0294206 A1 * | 11/2008 | Choi ................ A61B 17/708 606/86 A |
| 2009/0124861 A1 | 5/2009 | Fetzer |
| 2009/0228053 A1 | 9/2009 | Kolb et al. |
| 2010/0113885 A1 | 5/2010 | McBride et al. |
| 2010/0212460 A1 * | 8/2010 | Buss ................ A61B 17/7091 81/57.39 |
| 2011/0077689 A1 | 3/2011 | Mickiewicz |
| 2011/0196426 A1 | 8/2011 | Peukert et al. |
| 2012/0029580 A1 * | 2/2012 | Solitario, Jr. ...... A61B 17/7083 606/86 A |
| 2012/0035668 A1 | 2/2012 | Manninen et al. |
| 2012/0203279 A1 | 8/2012 | Walters |
| 2013/0096624 A1 * | 4/2013 | Di Lauro ............ A61B 17/7032 606/279 |
| 2013/0211453 A1 | 8/2013 | Lenke |
| 2013/0245694 A1 | 9/2013 | Choi |
| 2014/0039556 A1 | 2/2014 | Rutschmann |
| 2014/0039567 A1 | 2/2014 | Hoefer |
| 2014/0046372 A1 | 2/2014 | Ibrahim |
| 2014/0100618 A1 | 4/2014 | Kolb |
| 2014/0114354 A1 | 4/2014 | May |
| 2014/0163617 A1 | 6/2014 | Boachie-Adjei |
| 2014/0188182 A1 | 7/2014 | Chao et al. |
| 2014/0194939 A1 | 7/2014 | Seelig |
| 2014/0277170 A1 | 9/2014 | Barrett |
| 2014/0316475 A1 * | 10/2014 | Parikh ................ A61B 17/7085 606/86 A |

FOREIGN PATENT DOCUMENTS

| | | |
|---|---|---|
| JP | 2011514830 A | 5/2011 |
| JP | 2014534009 A | 12/2014 |

* cited by examiner

ORTHOPEDIC DEROTATION DEVICES AND METHODS OF INSTALLATION THEREOF

REFERENCE TO RELATED APPLICATIONS

The present application is a continuation of U.S. patent application Ser. No. 16/015,770 which is a continuation of U.S. Ser. No. 15/598,572, filed May 18, 2017, which is a continuation application of U.S. Ser. No. 14/665,273, filed Mar. 23, 2015, now U.S. Pat. No. 9,681,899, which are hereby incorporated by reference in their entireties for all purposes.

FIELD OF THE INVENTION

The present disclosure relates to orthopedic derotation devices and methods used to install these devices.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. One general example of a spinal irregularity is an abnormal curvature of the spine, for example, as exhibited with scoliosis, kyphosis, and/or lordosis. Scoliosis, a side-to-side curvature of the spine, can affect the dimensions of an individual's chest area, thereby impacting performance of internal organs such as the lungs and heart.

Treatment of irregular spinal curvatures can include, for example, reducing the severity and preventing further progression of the irregularity through physical therapy, bracing, and/or surgery. Surgical procedures can include realigning or correcting the curvature of the spine and optionally placing one or more rods alongside thereof to maintain the alignment.

SUMMARY OF THE INVENTION

Some embodiments herein are directed to a derotation system that can include first, second, and third derotation towers, wherein each derotation tower comprises a proximal derotation tube coupled to a distal engagement assembly that is configured to engage an anchor member; first and second clamp members, wherein each clamp member is configured to receive at least two derotation tubes; and a handle assembly configured to engage one of the clamp members; wherein the first clamp member is configured to couple the first and second derotation tubes along a first axis and the second clamp member is configured to couple the first and third derotation tubes along a second axis that is skewed relative to the first axis.

Other embodiments herein are directed to a derotation system that can include a plurality of derotation towers, wherein each derotation tower comprises a derotation tube; a plurality of clamp members each having a longitudinal axis, wherein each clamp member is configured to engage at least two derotation tubes; and a handle assembly configured to engage one of the clamp members; wherein, when the clamp members are engaged with the derotation tubes, the longitudinal axes of at least two clamp members are skewed.

Yet other embodiments herein are directed to a derotation kit that can include a plurality of derotation towers, wherein each derotation tower comprises a proximal derotation tube; a plurality of clamp members, wherein each clamp member is configured to engage at least two derotation tubes; a plurality of handle assemblies, wherein each handle assembly is configured to engage a clamp member; and a plurality of countertorque devices, wherein each countertorque device is configured to engage at least one derotation apparatus.

Some embodiments herein are directed to a method of installing a derotation system that can include engaging a plurality of derotation towers with a plurality of anchor members, wherein each derotation tower comprises a proximal derotation tube coupled to a distal engagement assembly; clamping a first clamp member around a first group of at least two derotation tubes along a first axis; clamping a second clamp member around a second group of at least two derotation tubes along a second axis, wherein the second axis is skewed relative to the first axis; coupling a handle assembly to one of the first and second clamp members; and applying force to the handle assembly to adjust a position of at least one derotation tower.

Other embodiments herein are directed to a method of installing a derotation system that can include engaging a plurality of derotation towers with a plurality of anchor members to thereby push at least one elongate rod into engagement with the anchor members, wherein each derotation tower comprises a proximal derotation tube coupled to a distal engagement assembly; clamping a first clamp member around a first group of at least two derotation tubes along a first axis; clamping a second clamp member around a second group of at least two derotation tubes along a second axis, wherein the second axis is skewed relative to the first axis; coupling a handle assembly to one of the first and second clamp members; and applying force to the handle assembly to adjust a position of at least one derotation tower.

Still other embodiments herein are directed to a method of installing a derotation system that can include providing a plurality of anchor members and a plurality of derotation towers; engaging each derotation tower with a different anchor member; clamping each derotation tower to at least two other derotation towers along first and second axes that are skewed relative to each other; and applying force to the system to adjust a position thereof.

Further areas of applicability of the present disclosure will become apparent from the detailed description provided hereinafter. It should be understood that the detailed description and specific examples, while indicating certain embodiments, are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
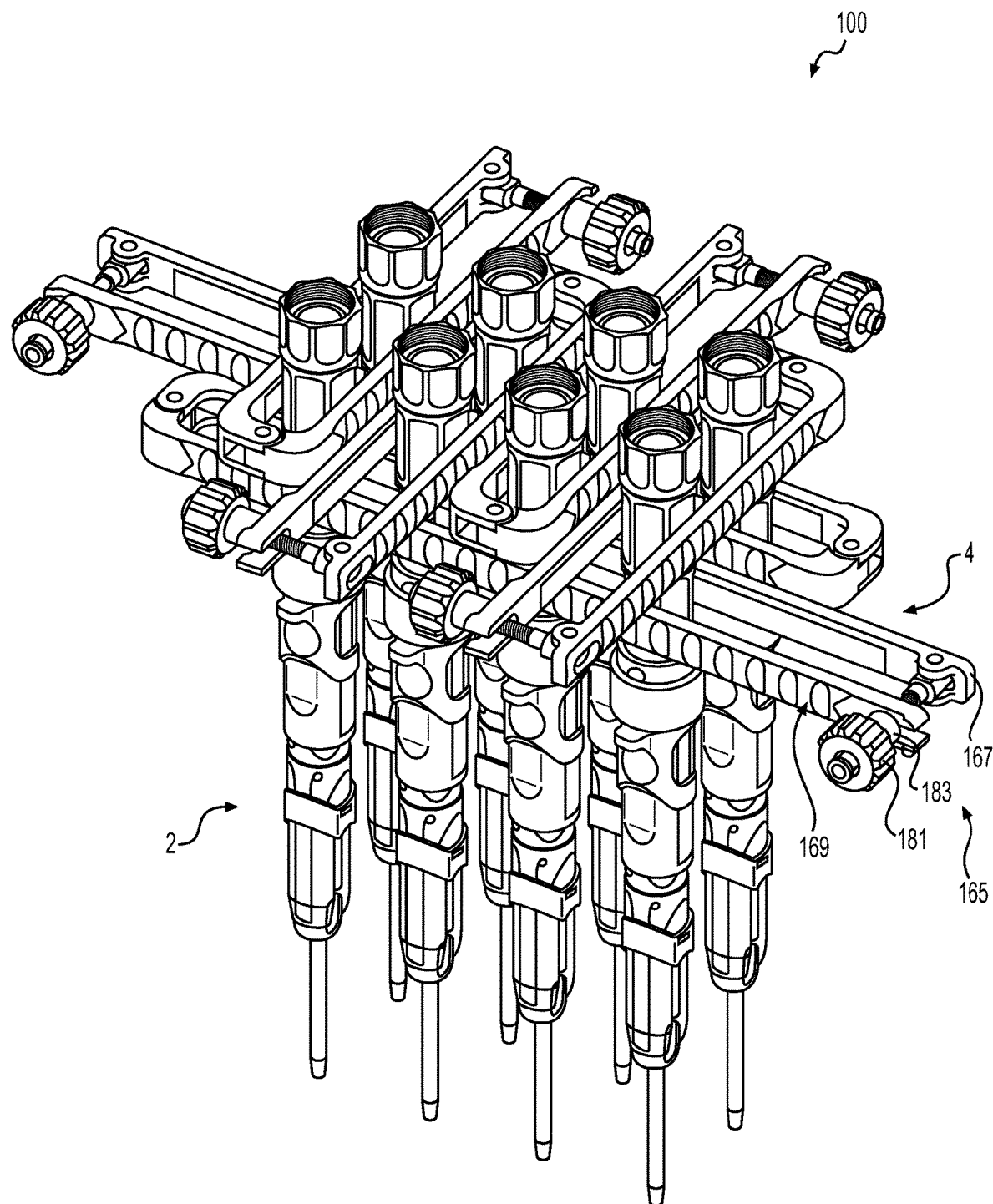
FIG. 1 illustrates a perspective view of a derotation system as described herein.

In some procedures to treat irregular spinal curvatures, a surgeon or other user may attach bone anchors to select vertebrae of the spine. A rod can be inserted through the bone anchors to adjust or maintain the relative positions of the vertebrae, thereby promoting correction of the curvature. A mechanical force can be used to deliver the rod to the bone anchors in a process that may be referred to as reduction. In some instances, a locking member, such as a set screw or locking cap, can be coupled with the bone anchor to retain the rod therein. In addition to adjusting for curvature, the angular rotation of one or more vertebrae relative to other vertebrae can be adjusted. This process can involve rotating the anchors and/or rods via tube members and can be referred to as derotation. Accordingly, described herein are derotation systems and components thereof that can be advantageously used to manipulate and/or adjust the rotational angle of one or more vertebrae.

Components of all of the systems and devices disclosed herein can be made of materials known to those skilled in the art, including metals (e.g., titanium), metal alloys (e.g., stainless steel, titanium alloys, and/or cobalt-chromium alloys), ceramics, polymers (e.g., poly ether ether ketone (PEEK), polyphenylene sulfone (PPSU), polysulfone (PSU), polycarbonate (PC), polyetherimide (PEI), polypropylene (PP), polyacetals, or mixtures or co-polymers thereof), allograft, and/or combinations thereof. In some embodiments, the systems and devices may include radiolucent and/or radiopaque materials. In some embodiments, the systems and devices may be formed of silicone rubber. In other embodiments, one or more components may be coated with a bone growth-enhancing material, such as hydroxyapatite. The components can also be machined and/or manufactured using techniques known to those skilled in the art. For example, polymeric components may be injection-molded or blow-molded.

Embodiments herein are directed to derotation systems that can include one or more derotation towers and/or clamp members. The clamp members may be configured to couple, clamp, and/or link the derotation towers together to form the derotation system. In some embodiments, the derotation systems can additionally include one or more handle assemblies and/or countertorque devices. Advantageously, those skilled in the art may appreciate that the derotation systems of the present disclosure may include any combination of any embodiments of derotation towers, clamp members, handle assemblies, and/or countertorque devices described herein. The derotation systems may be configured to adjust the curvature and/or rotation of a patient's spine in a derotation procedure, as described herein. In some embodiments, the derotation systems may also be configured to reduce a rod, e.g., to push a rod into engagement with an anchor member, such as a tulip head or pedicle screw. The derotation towers may advantageously be cannulated to allow passage of a fastener, such as a set screw or locking cap, therethrough. In use, after the spine is derotated, the fastener may be passed through the derotation tower to couple with an anchor member, thereby securing the anchor member to a rod and/or at a particular angle.

The derotation towers described herein can each include a proximal derotation tube coupled to and/or extending from a distal engagement assembly. The derotation tube can include a longitudinal axis and a variable (e.g., angled, non-smooth, abrasive, roughened, increased-friction, coarse, grainy, sandblasted, knurled, texturized, bumpy, ridged, toothed, and/or irregular) transverse (e.g., circumferential) outer surface thereabout. The derotation tube can include a cannula extending entirely therethrough along the longitudinal axis thereof. The longitudinal axis can be a straight or curved line. The distal engagement assembly can be configured to engage an anchor member (e.g., a bone anchor such as a pedicle screw or hook, alone or in combination with a housing, such as a tulip head, and/or an elongate rod). The systems disclosed herein can include a plurality of derotation towers, e.g., 2, 3, 4, 5, 6, 7, 8, or more towers. In some embodiments, the systems disclosed herein can include at least first, second, and third derotation towers.

Figure 2:
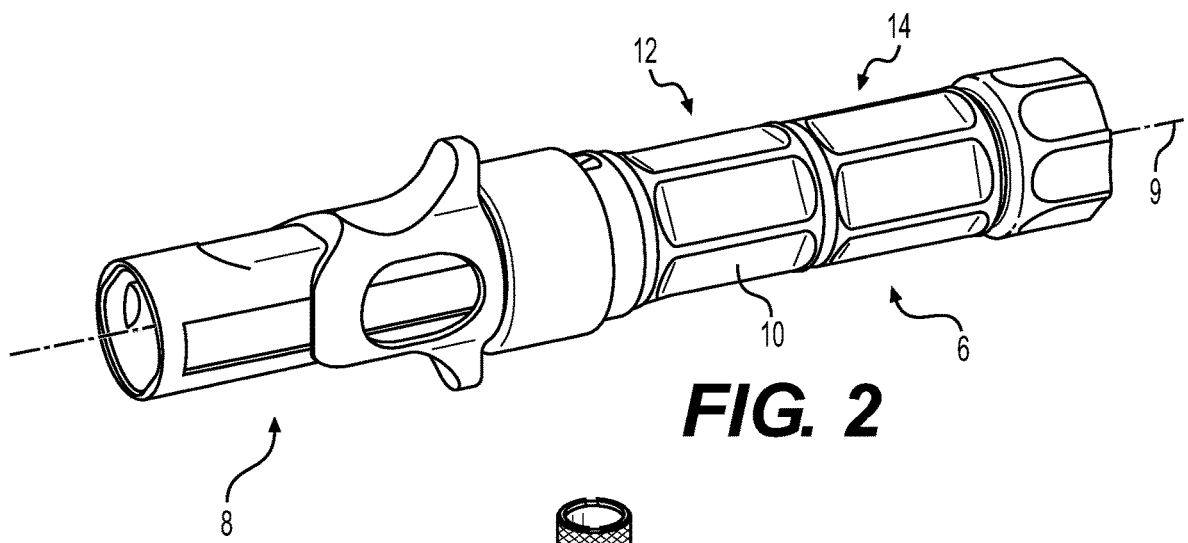
FIG. 2 illustrates a perspective view of a derotation tube and a distal engagement assembly as described herein.

Turning now to FIG. 1, some embodiments herein are directed to a derotation system 100 that can include one or more derotation towers, such as derotation tower 2, and one or more clamp members, such as clamp member 4. As illustrated in FIG. 2, derotation tower 2 can include a proximal derotation tube 6 and a distal engagement assembly 8. The proximal derotation tube 6 can include a longitudinal axis 9 and a variable transverse outer surface thereabout. As illustrated in FIG. 2, the derotation tube 6 can include a plurality of angled surfaces 10. In some embodiments, the derotation tube 6 can include six angled surfaces (e.g., can include a hexagonal outer surface or transverse outer cross-section). In other embodiments, the derotation tube 6 can include 3, 4, 5, 6, 7, 8 or more angled surfaces. In some embodiments, the derotation tube 6 can include first and second rotatable members 12, 14. The first and second rotatable members 12, 14 can be positioned in series along the longitudinal axis 9. Each of the first and second rotatable members 12, 14 can include a variable outer surface. For example, each of the first and second rotatable members 12, 14 can include a hexagonal outer surface or transverse outer cross-section. The first and second rotatable members 12, 14 may be advantageously configured to rotate relative to each other. In some embodiments, the derotation tube 6 can further include a locking member configured to lock the rotational orientation of the first and/or second rotatable members 12, 14. Advantageously, the first and second rotatable members 12, 14 can be configured to each couple to a clamp member along a different axis, as illustrated in FIG. 1. Each rotatable member 12, 14 can be rotated individually to adjust and/or accommodate the orientation of the clamp member.

Figure 3:
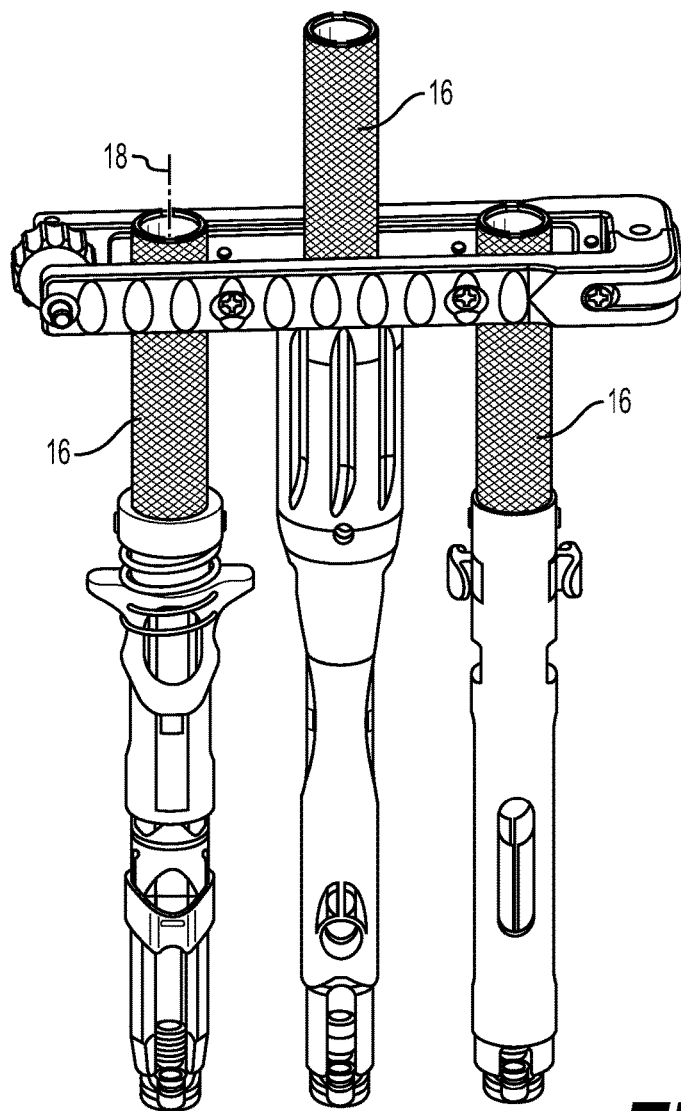
FIG. 3 illustrates a perspective view of a clamp member and three derotation towers as described herein.

An alternative embodiment of a proximal derotation tube is proximal derotation tube 16, illustrated in FIG. 3. Derotation tube 16 can include a longitudinal axis 18 and a variable transverse outer surface thereabout. In these embodiments, derotation tube 16 may be a unitary (e.g., one-piece) tube. As illustrated in FIG. 3, at least a section of the variable transverse outer surface of the derotation tube 16 can include roughening and/or texturizing (e.g., knurling). In some embodiments, derotation tube 16 may be referred to as a knurled tube.

In some embodiments, the proximal derotation tube and the distal engagement assembly, or a component thereof, may form a unitary body. In other embodiments, the proximal derotation tube may be reversibly or irreversibly coupled to the distal engagement assembly. For example, in some embodiments the proximal derotation tube may be welded to the distal engagement assembly. In other embodiments, the proximal derotation tube may be clipped, threaded, snapped, bolted, and/or otherwise coupled to the distal engagement assembly. In embodiments where the distal engagement assembly includes two or more components (e.g., an inner sheath and an outer sheath), the proximal derotation tube may be coupled with any of the components.

Figure 4A:
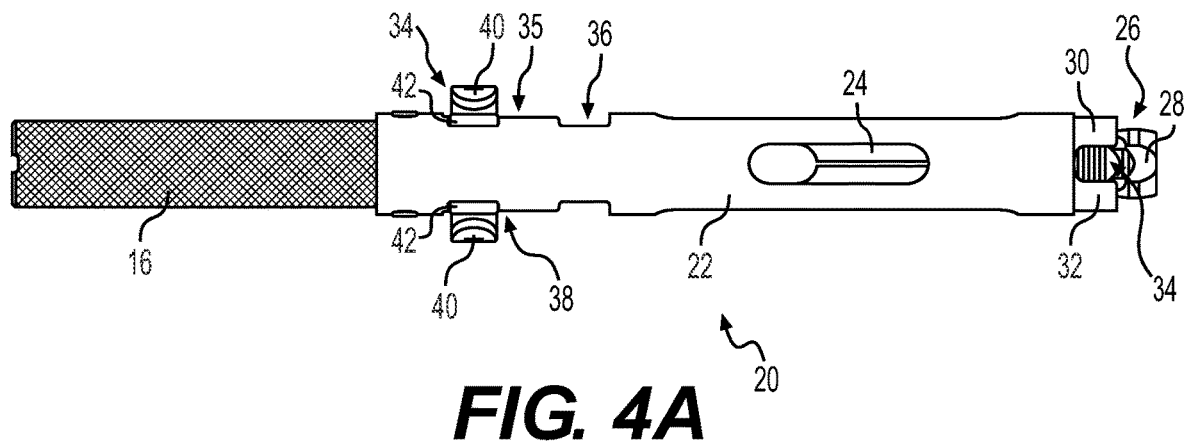
FIGS. 4A-B illustrate perspective views of derotation towers as described herein.

One embodiment of a distal engagement assembly, distal engagement assembly 20, is illustrated in FIG. 4A. The distal engagement assembly 20 can include an outer sleeve 22 slideably disposed over an inner sleeve 24. The inner sleeve 24 can include a distal end 26 configured to engage an anchor member 28. As illustrated in FIG. 4A, the distal end 26 of the inner sleeve 24 can include two tips 30, 32 separated by a longitudinal slot 34. Each tip 30, 32 may also include a beveled protrusion (not shown) extending radially outwards and that may be configured to engage an inner surface of the outer sleeve 22.

The outer sleeve 22 may include a channel 38 at a proximal end having an enlarged proximal opening 34 and an enlarged distal opening 36. The proximal opening 34 and the distal opening 36 may each have a width that is greater than that of an intermediate portion 35 therebetween. For example, the channel 38 may be generally "I"-shaped. As illustrated in FIG. 4A, the channel 38 may pass entirely through the outer sleeve 22 in a transverse direction. In some embodiments, the proximal end of the outer sleeve 22 may also include one, two, or more flat exterior sections. In some embodiments, the outer sleeve 22 can include two parallel flat exterior sections (e.g., two parallel walls). The flat exterior sections may be configured to couple with one or more installation tools, such as a countertorque device, described further herein.

The distal engagement assembly 20 can also include an actuator 40. Actuator 40 may be coupled to a stop 42. The stop 42 may be sized to fit within the enlarged proximal and distal openings 34, 36, but not within the intermediate portion 35. In use, when the actuator 40 is depressed, the distal engagement assembly 20 may transition between an unlocked position and a locked position, wherein in the locked position the distal engagement assembly 20 is coupled (e.g., secured) to and/or engaged with the anchor member 28. In the locked position, illustrated in FIG. 4A, the stop 42 may be positioned within the proximal opening 34 and the outer sleeve 22 may engage the beveled protrusion (not shown) on each tip 30, 32. In this position, the outer sleeve 22 may be applying a radial force on the beveled protrusions, causing the slot 34 to compress, bringing the tips 30, 32 together to clamp the anchor member 28 therebetween. To transition to the unlocked position, e.g., to disengage the distal engagement assembly 20 from the anchor member 28, the actuator 40 may be depressed (e.g., squeezed), disengaging the stop 42 from the proximal opening 34. The outer sleeve 22 may then be translated proximally until the beveled protrusions are uncovered and the stop 42 is aligned with the distal opening 36. The actuator 40 may then be released to allow the stop 42 to be retained within the distal opening 36. To transition to the locked position, e.g., to engage the distal engagement assembly 20 with the anchor member 28, the actuator 40 may be depressed (e.g., squeezed), disengaging the stop 42 from the distal opening 36. The outer sleeve 22 may then be translated distally until the beveled protrusions are covered and the stop 42 is aligned with the proximal opening 34. The actuator 40 may then be released to allow the stop 42 to be retained within the proximal opening 34.

Figure 4B:
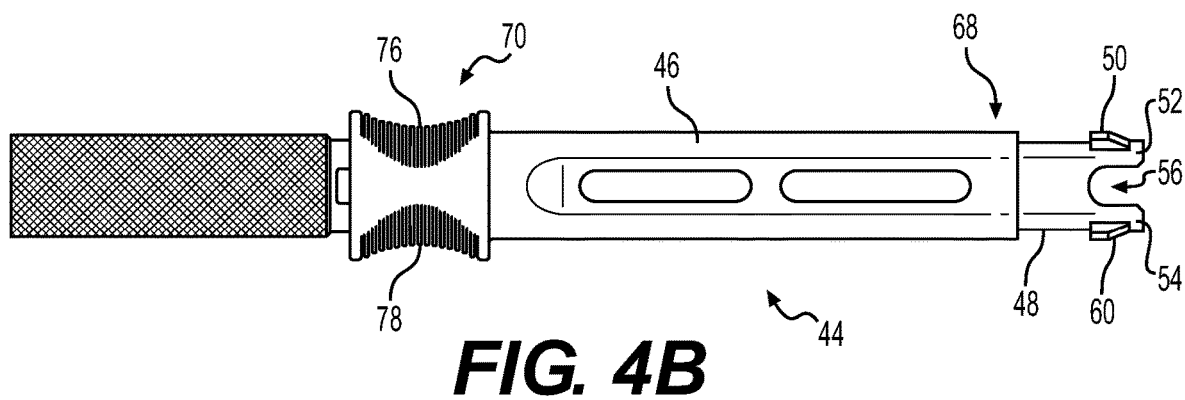
Figure 4C:
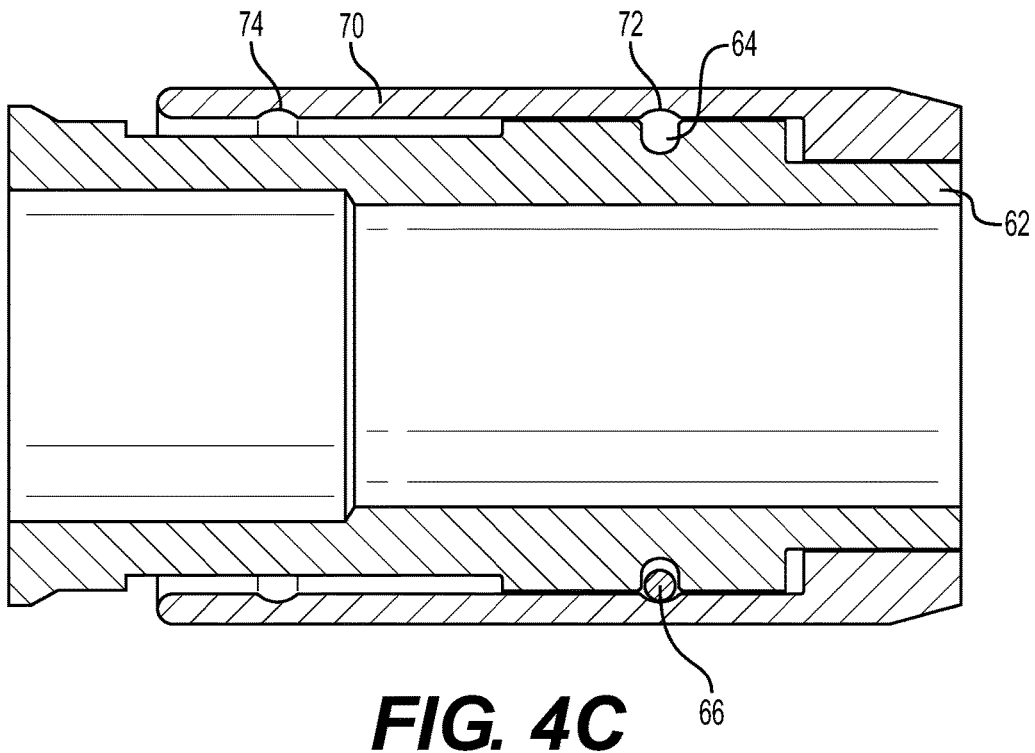
FIG. 4C illustrates a cross-sectional view of the locking mechanism of the derotation tower illustrated in FIG. 4B.

Another embodiment of a distal engagement assembly, distal engagement assembly 44, is illustrated in FIGS. 4B-C. The distal engagement assembly 44 can include an outer sleeve 46 slideably disposed over an inner sleeve 48. The inner sleeve 48 can include a distal end 50 configured to engage an anchor member (not shown). As illustrated in FIG. 4B, the distal end 50 of the inner sleeve 48 can include two tips 52, 54 separated by a longitudinal slot 56. Each tip 52, 54 may also include a protrusion 58, 60 extending radially outwards and that may be configured to engage an inner surface of the outer sleeve 46. The inner sleeve 48 may also include a proximal end 62, illustrated in FIG. 4C. The proximal end 62 may include a circumferential groove 64 on an outer surface thereof. The circumferential groove 64 may be configured to receive a retaining ring 66 therein. As illustrated in FIG. 4C, the retaining ring 66 may be configured to be disposed between the inner sleeve 48 and the outer sleeve 46. In some embodiments, the retaining ring 66 may be compressible and/or compliant.

The outer sleeve 46 may include a distal end 68 and a proximal end 70, as illustrated in FIGS. 4B-C. The distal end 68 may be configured to engage the protrusions 58, 60 of the inner sleeve 48. The proximal end 70 may include a distal circumferential groove 72 and a proximal circumferential groove 74, both extending along an inner surface thereof. As illustrated in FIG. 4B, the proximal end 70 may also include at least one or more concave gripping surfaces 76, 78. Each concave gripping surface 76, 78 may include an engagement or friction-increasing feature, such as ridges, teeth, knurling, and/or sandblasting. In some embodiments, the proximal end 70 may also include one, two, or more flat exterior sections. In some embodiments, the proximal end 70 can include two parallel flat exterior sections (e.g., two parallel walls). The flat exterior sections may be configured to couple with one or more installation tools, such as a countertorque device, described further herein.

In use, the distal engagement assembly 44 may transition between an unlocked position and a locked position, wherein in the locked position the distal engagement assembly 44 is coupled (e.g., secured) to and/or engaged with an anchor member (not shown). Although not illustrated, those skilled in the art may appreciate that an anchor member (e.g., a bone screw engaged with a housing and/or a rod) may be positioned between the tips 52, 54 prior to transitioning the distal engagement assembly from the unlocked position to the locked position. In the unlocked position, illustrated in FIG. 4B-C, the protrusions 58, 60 at the distal end 50 of the inner sleeve 48 may be exposed (e.g., not engaged with the outer sleeve 46). Additionally, the retaining ring 66 may rest within the groove 64 on the proximal end 62 of the inner sleeve 48 and the distal groove 72 on the proximal end 70 of the outer sleeve 46. In some embodiments, the groove can be circumferential or rectangular. The retaining ring 66 may inhibit the outer sleeve 46 from translating axially. To transition to the locked position, e.g., to engage the distal engagement assembly 44 with the anchor member, a user may grasp the concave gripping surfaces 76, 78 and translate or slide the outer sleeve 46 distally. The retaining ring 66 may be pushed and/or compressed into the circumferential groove 64, allowing the outer sleeve 46 to translate or slide. The outer sleeve 46 may continue to translate distally until the retaining ring 66 is aligned with the proximal groove 74 and the distal end 68 of the outer sleeve 46 has engaged the protrusions 58, 60. When the retaining ring 66 is aligned with the proximal groove 74, it may move and/or expand into the proximal groove 74, thereby inhibiting the outer sleeve 46 from translating axially. In this position, the distal end 68 of the outer sleeve 46 may be applying a radial force on the protrusions 58, 60, causing the slot 56 to compress, bringing the tips 52, 54 together to clamp the anchor member (not shown) therebetween.

In some embodiments, the distal engagement assembly may include a rod reducer assembly which be configured to reduce a rod engaged with an anchor member (e.g., may be configured to urge a rod towards the anchor member or portion thereof). Some embodiments may include rod reducer assembly 80, illustrated in FIG. 5A. Rod reducer assembly 80 may include a connector member 82 and a clip reducer 84 configured to be reversibly coupled with the connector member 82. The rod reducer assembly 80 may also include a threaded driver (not shown).

Figure 5A:
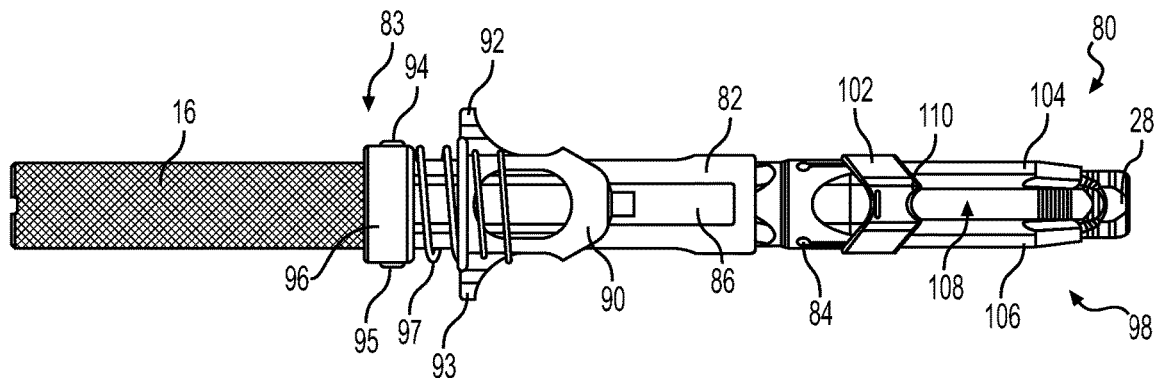
FIG. 5A illustrates a perspective view of a derotation tower that includes a rod reducer assembly as described herein.
Figure 5B:
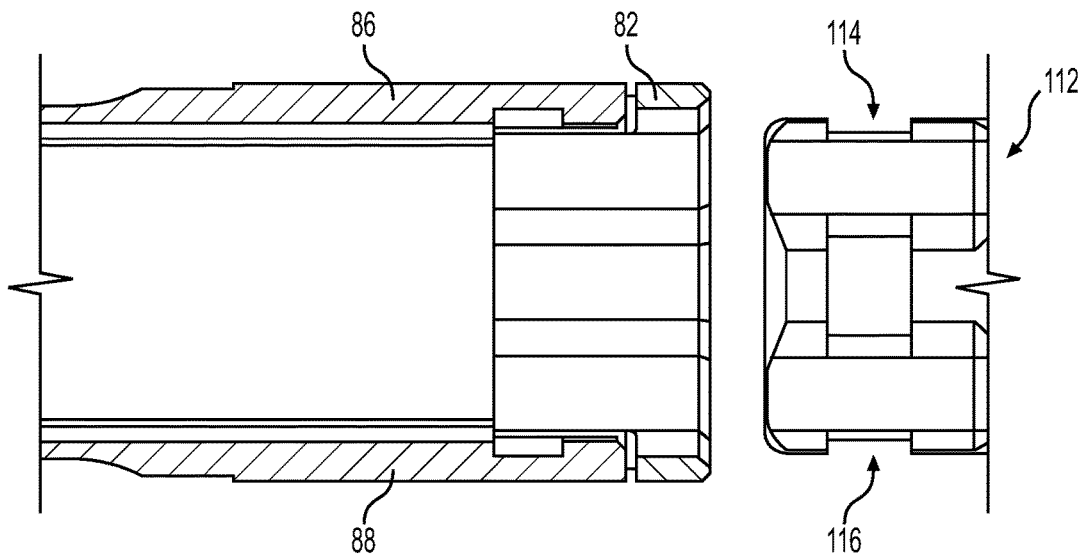
FIG. 5B illustrates the coupling mechanism of components of the rod reducer assembly illustrated in FIG. 5A.

The connector member 82 may be a generally tubular body having a cannula extending longitudinally therethrough. The connector member 82 may include a proximal end 83 that is coupled to the derotation tube 16. The proximal end 83 may also include a collar 96. The collar 96 may be generally cylindrical with two flat exterior sections 94, 95 (e.g., two parallel walls). The flat exterior sections 94, 95 may be configured to couple with one or more installation tools, such as a countertorque device, described further herein. The connector member 82 may include a first cantilevered tab 86 and a symmetrical second cantilevered tab 88 on an opposite side of the connector member 82, as illustrated in FIG. 5B. The tabs may protrude radially outward from an outer surface of the connector member 82 as well as inward from an inner surface thereof. As illustrated in FIG. 5A, rod reducer assembly 80 may also include a handle member 90 having a cannula extending longitudinally therethrough and two arms 92, 93 extending transversely therefrom. The connector member 82 may be received within the cannula of the handle member 90. The handle member 90 may have an inner surface configured to engage an outer surface of the tabs 86, 88. The handle member 90 may be coupled to the proximal end 83 of the connector member 82 by a spring member 97, such as a compression spring.

The clip reducer 84 may be cannulated and may include a distal end 98 configured to engage anchor member 28. As illustrated in FIG. 5A, the distal end 98 can include two tips 104, 106 separated by a longitudinal slot 108. The clip reducer 84 may be configured to receive the anchor member 28 between the two tips 104, 106. Each tip 104, 106 may also include a protrusion (not shown) extending radially outwards and that may be configured to engage an inner surface of a reduction member 102. The reduction member 102 may be slideably engaged with the clip reducer 84. The reduction member 102 may be a tubular member having a cannula extending therethrough, and may include a distally-extending tip 110. In some embodiments, the reduction member 102 may be generally chevron- or V-shaped when viewed from a side. The tip 110 may include a partially-circular (e.g., concave) cut-out configured to engage, nest, or abut a cylindrical rod. The clip reducer 84 may be received within the cannula of the reduction member 102. The reduction member 102 may be configured to slide longitudinally (e.g., distally and/or proximally) along the clip reducer 84. The clip reducer 84 may also include a proximal end 112, as illustrated in FIG. 5B. The proximal end 112 may include depressions or recesses 114, 116 that can be configured to receive at least a portion of tabs 86, 88 therein. The rod reducer assembly 80 may further include an elongate threaded driver (not shown). The driver may be configured to engage and/or actuate the reduction member 102.

In use, the connector member 82 may be coupled with the clip reducer 84 as follows. The arms 92, 93 of the handle member 90 may be grasped and the handle member 90 pulled proximally towards the collar 96 to compress the spring member 97 and release the tabs 86, 88. The proximal end 112 of the clip reducer 84 may be inserted into a distal end of the connector member 82 until the recesses 114, 116 are aligned with the tabs 86, 88. The arms 92 of the handle member 90 may then be released, thereby releasing the spring member 96 and causing the handle 90 to return to its distal position. The inner surface of the handle 90 may engage the tabs 86, 88, pushing them radially inwards and into the recesses 114, 116. The handle 90 may retain the tabs 86, 88 within the recesses 114, 116 and may thereby inhibit the connector member 82 from disengaging from the clip reducer 84.

To engage rod reducer assembly 80 with an anchor member, the distal end 98 of the clip reducer 84 may be positioned or placed around at least a portion of the anchor member 28. The clip reducer 84 may be placed around anchor member 28 before or after coupling with the connector member 82. Although not illustrated in FIG. 5A, those skilled in the art may appreciate that, in use, anchor member 28 may include an elongate rod resting in the U-shaped opening thereof. To reduce the rod, e.g., to urge the rod into closer and/or secure engagement with the anchor member 28, the threaded driver or screw may be threaded through the clip reducer 84. Rotation of the threaded driver, which is in engagement with the reduction member 102, can cause the reduction member 102 to translate distally. As the reduction member 102 translates distally, it may apply a radial force on the tips 104, 106, compressing the slot 108 and causing the tips 104, 106 to clamp the anchor member 28 therebetween. The threaded driver may urge the reduction member 102 to translate distally until it abuts the elongate rod (not shown) and urges or pushes the elongate rod into engagement with the anchor member 28.

Figure 5C:
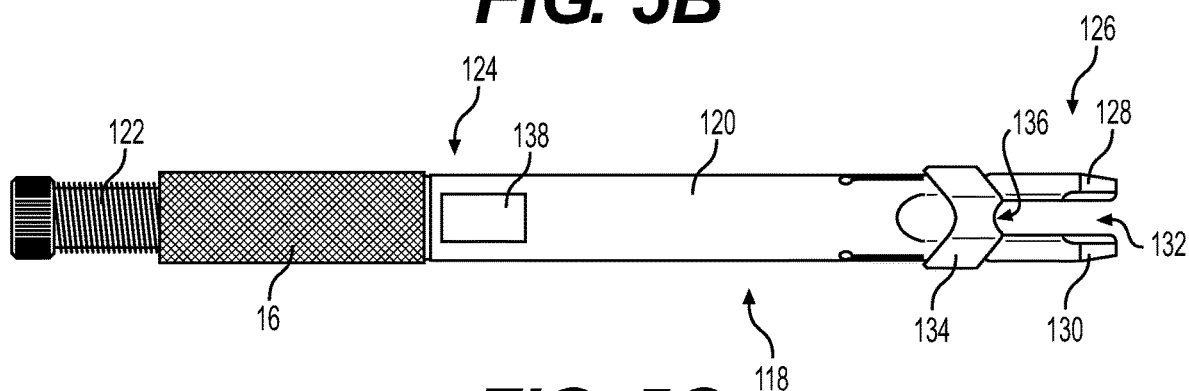
FIGS. 5C-D illustrate perspective views of derotation towers that each include a rod reducer assembly as described herein.

FIG. 5C illustrates another embodiment of a rod reducer assembly. Rod reducer assembly 118 may include a clip reducer 120 and a threaded driver 122. The clip reducer 120 can include a proximal end 124 and a distal end 126. The clip reducer 120 may be coupled to derotation tube 16 at the proximal end 124. The proximal end 124 may also include one, two, or more flat exterior sections 138. In some embodiments, the proximal end 124 can include two parallel flat exterior sections (e.g., two parallel walls). The flat exterior sections 138 may be configured to couple with one or more installation tools, such as a countertorque device, described further herein. The distal end 126 may include two tips 128, 130 separated by a longitudinal slot 132. The rod reducer assembly 118 may also include a reduction member 134 that is slideably engaged with the clip reducer 120. The reduction member 134 may be a tubular member having a cannula extending therethrough, and may include a distally-extending tip 136. In some embodiments, the reduction member 134 may be generally chevron- or V-shaped when viewed from a side. The tip 136 may include a partially-circular (e.g., concave) cut-out configured to engage or abut a cylindrical rod. The clip reducer 120 may be received within the cannula of the reduction member 134. The reduction member 134 may be configured to translate or slide longitudinally (e.g., distally and/or proximally) along the clip reducer 120.

The threaded driver 122 may be configured to be received within the cannula of the clip reducer 120 and may be configured to engage the reduction member 134. To engage rod reducer assembly 118 with an anchor member, the distal end 126 or a portion thereof may be placed or positioned around an anchor member. In use, the tips 128, 130 may be placed around an anchor member that may include, for example, a housing and a fastener (e.g., a pedicle screw or hook) therein. An elongate rod may also be placed or positioned at or within the housing. To reduce the rod, e.g., to urge the rod into closer engagement with the anchor member, the threaded driver 122 may be inserted (e.g., threaded) through the clip reducer 120 from a proximal end of the derotation tube 16 and into engagement with the reduction member 134. The threaded driver 122 may actuate the reduction member 134, causing it to translate distally. As the reduction member 134 translates distally, it may apply a radial force on the tips 128, 130, compressing the slot 132 and causing the tips 128, 130 to clamp the anchor member therebetween. The threaded driver 122 may urge the reduction member 134 to translate distally until it abuts the elongate rod (not shown) and urges or pushes the elongate rod into engagement with the anchor member.

Figure 5D:
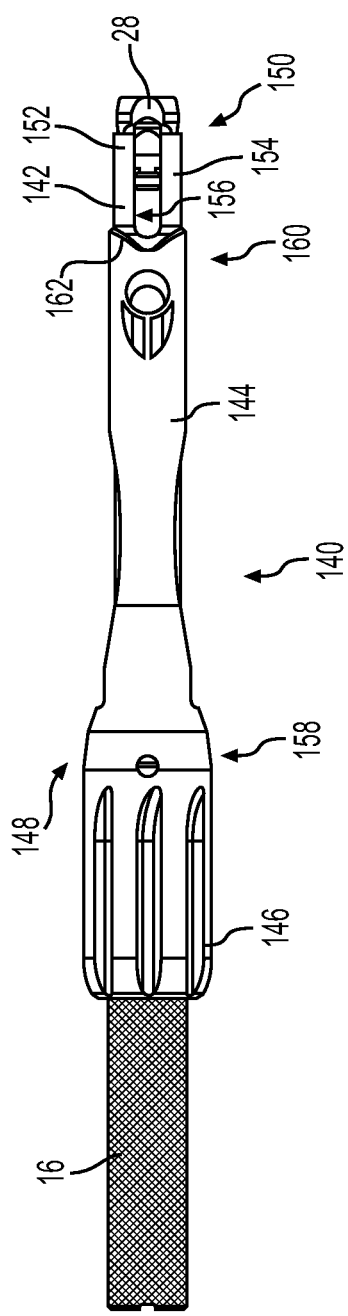

FIG. 5D illustrates another embodiment of a rod reduction assembly. Rod reduction assembly 140 can include an inner sleeve 142, an outer sleeve 144, and a rotatable handle 146. The inner sleeve 142 may include a proximal end 148 and a distal end 150. The proximal end 148 may be configured to couple with derotation tube 16. The inner sleeve 142 may be configured to engage anchor member 28. In some embodiments, the distal end 150 can include two or more tips 152, 154 (e.g., four or more) separated by a longitudinal slot 156. The inner sleeve 142 may be configured to receive the anchor member 28 between the two tips 152, 154. Each tip 152, 154 may also include a protrusion (not shown) extending radially outwards and that may be configured to engage an inner surface of the outer sleeve 144.

The outer sleeve 144 may be slideably disposed over the inner sleeve 142 and may be configured to reduce an elongate rod (not shown). The outer sleeve 144 may include a proximal end 158 and a distal end 160. The distal end 160 may include a distal tip 162 having a partially-circular (e.g., concave) cut-out configured to engage, nest, or abut a cylindrical rod. The proximal end 158 may include one, two, or more flat exterior sections. In some embodiments, the proximal end 158 can include two parallel flat exterior sections (e.g., two parallel walls). The flat exterior sections may be configured to couple with one or more installation tools, such as a countertorque device, described further herein. The proximal end 158 may be engaged or coupled with the rotatable handle 146. The rotatable handle 146 may be configured to actuate the outer sleeve 144.

To engage rod reducer assembly 140 with anchor member 28, the distal end 150 or a portion thereof may be placed or positioned around the anchor member 28. In use, the tips 152, 154 may be placed around anchor member 28 (e.g., a tulip head or other housing). Although not illustrated in FIG. 5D, those skilled in the art may appreciate that, in use, anchor member 28 may include an elongate rod resting in the U-shaped opening thereof. To reduce the rod, e.g., to urge the rod into closer and/or secure engagement with the anchor member 28, the rotatable handle 146 may be rotated (e.g., threaded onto the inner sleeve 142) to actuate the outer sleeve 144, thereby urging and/or pushing the outer sleeve 144 in a distal direction. As the outer sleeve 144 translates distally, it may apply a radial force on the tips 152, 154, compressing the slot 156 and causing the tips 152, 154 to clamp the anchor member 28 therebetween. The rotatable handle 146 may continue to rotate, urging the outer sleeve 144 to translate distally until it abuts the elongate rod (not shown) and urges or pushes the elongate rod into engagement with the anchor member 28.

The derotation systems disclosed herein may also include first, second, or more clamp members. In some embodiments, each clamp member may be configured to engage, couple, and/or receive (e.g., clamp) at least two derotation towers or portions thereof (e.g., proximal derotation tube and/or distal engagement assembly). For example, each clamp member may be configured to engage, couple, and/or receive (e.g., clamp) at least two derotation tubes. Thus, the derotation systems described herein may include a plurality of clamp members and derotation tubes. Any combination of embodiments of clamp members, derotation towers, and/or derotation tubes may be used in the derotation systems described herein. In some embodiments that include a plurality of (e.g., two or more) clamp members engaged with a plurality of derotation tubes, the longitudinal axes of at least two clamp members may be skewed (e.g., the longitudinal axes would intersect if in the same plane). In some embodiments, the derotation system can include at least three (e.g., first, second, and third) derotation towers and at least two (e.g., first and second) clamp members. In these embodiments, the first clamp member may be configured to couple two (e.g., first and second) derotation tubes along a first axis and the second clamp member may be configured to couple two (e.g., first and third) derotation tubes along a second axis, wherein the second axis is skewed relative to the first axis (e.g., the first and second axes would intersect if in the same plane). In other embodiments, the clamp members may be configured to engage each derotation tower in the system with at least a first adjacent derotation tower along a first axis and at least a second adjacent derotation tower along a second axis, wherein the second axis is skewed relative to the first axis. One such example is illustrated in FIG. 1.

Figure 6A:
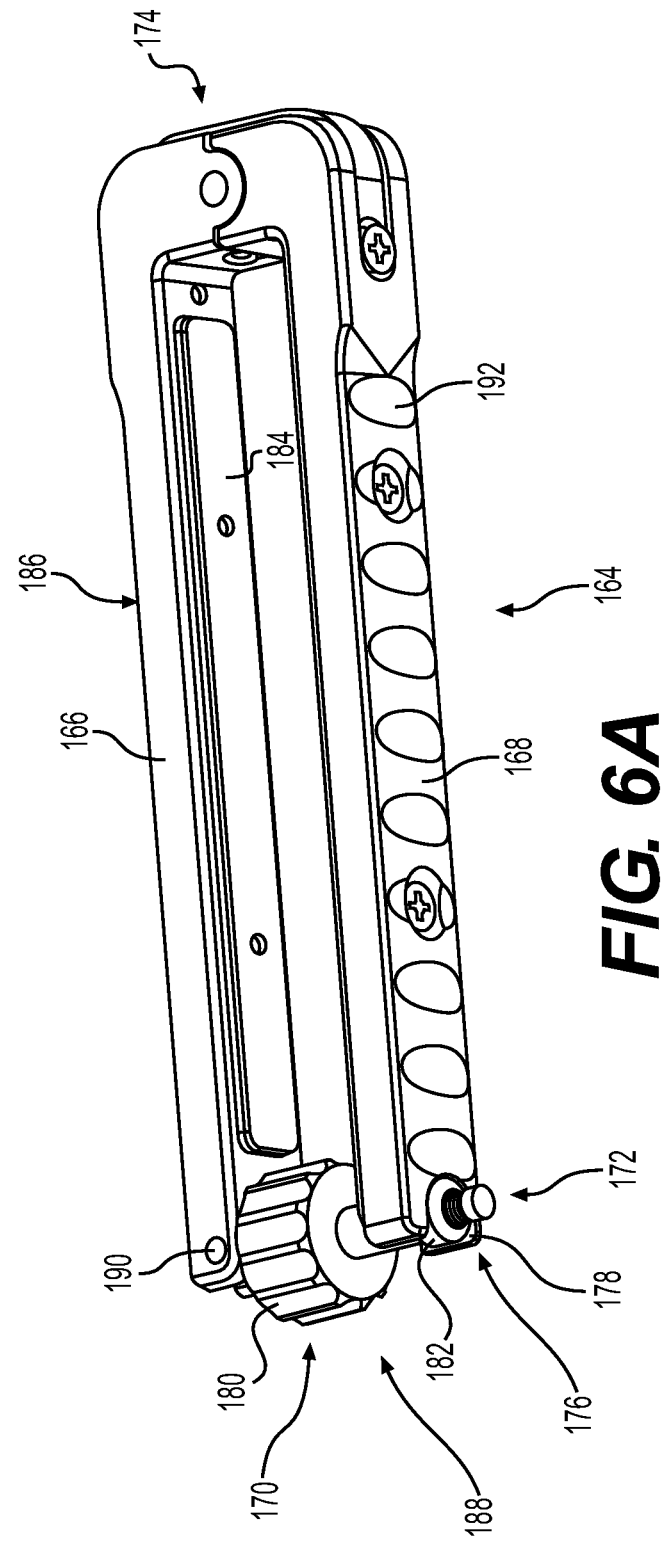
FIG. 6A illustrates a perspective view of a clamp member as described herein.

FIG. 6A illustrates one embodiment of a clamp member. Clamp member 164 can include a first elongate arm 166 and a second elongate arm 168. The first elongate arm 166 can be coupled to an actuator assembly 170 and the second elongate arm can include a receiving portion 172 extending therefrom. Clamp member 164 can also include a first end 174 and a second end 188, wherein the first and second arms 166, 168 may be coupled together at the first end 174. Clamp member 164 may include a longitudinal axis that extends between the first and second ends 174, 188.

The first arm 166 can include an inner surface 184 and an outer surface 186, wherein the inner surface 184 is closer to the second arm 168 and the outer surface 186 is farther from the second arm 168. As illustrated in FIG. 6A, the term "inner surface" can refer to a surface attached to the first arm 166, as well as to the direct surface of the first arm 166. The inner surface 184 can advantageously include a retaining (e.g., friction-increasing) feature. In some embodiments, the inner surface 184 may include a variable surface feature, and may be, for example, angled, non-smooth, abrasive, roughened, increased-friction, coarse, grainy, sandblasted, knurled, texturized, bumpy, ridged, toothed, and/or irregular. As illustrated in FIG. 6A, the retaining feature of the inner surface 184 can include knurling. In other embodiments, the retaining feature may be soft, compressive, and/or compliant. For example, the retaining feature may be a polymeric (e.g., silicone) surface. In yet other embodiments, the retaining feature can include a scalloped surface, e.g., a plurality of indentations, wherein each indentation is configured to nest a portion of a derotation apparatus therein. The second arm 168 can also have an inner surface having some or all of the same features as the inner surface 184. As illustrated with respect to the second arm 168, in some embodiments the outer surface of either or both arms can include a plurality of curved depressions or indentations 192.

The first and second elongate arms 166, 168 may be pivotably coupled at the first end 174 of the clamp member 164. The first and second elongate arms 166, 168 may also be coupled to a spring member, such as a cantilever or torsion spring, at the first end 174. Thus, in use, when the arms 166, 168 are pulled apart and subsequently released, the spring member may pull the arms 166, 168 back towards each other.

The receiving portion 172 can include a receptacle 176 therein. At least a portion of the actuator assembly 170 may be configured to be reversibly received within the receptacle 176. In some embodiments, the receptacle 176 can be open on one side and can be, for example, a U-shaped channel or opening. In other embodiments, the receptacle may be a forked opening (e.g., may include two tines defining a channel therebetween). In yet other embodiments, the receptacle can include a tapered opening, e.g., such that the width of the opening of the receptacle is less than the diameter of the receptacle. In some embodiments, the receptacle 176 may have a constant diameter or width as measured longitudinally from the inner surface to the outer surface of the second arm 168. For example, the receptacle 176 may generally have the shape of a cylindrical segment. In other embodiments, the receptacle 176 may have a variable diameter or width. For example, the receptacle 176 may be tapered (e.g., conical or frustoconical). In some embodiments, the receptacle 176 can include a countersink configured to nest a portion of the actuator assembly 170 (e.g., head member 182) therein.

The actuator assembly 170 can include a threaded rod 178 and a threaded nut 180. The threaded nut 180 can be generally cylindrical and can include a threaded passageway configured to mate with the threaded rod 178. In some embodiments, the threaded nut 180 can include a gripping surface. For example, as illustrated in FIG. 6A, the threaded nut 180 can be texturized and can include a plurality of alternating ridges and valleys. In some embodiments, the threaded nut 180 can be coupled to a head member 182. The head member 182 can be configured to be received (e.g., locked) within the receptacle 176. The head member 182 may be configured to rotate within the receptacle 176.

Figure 10:
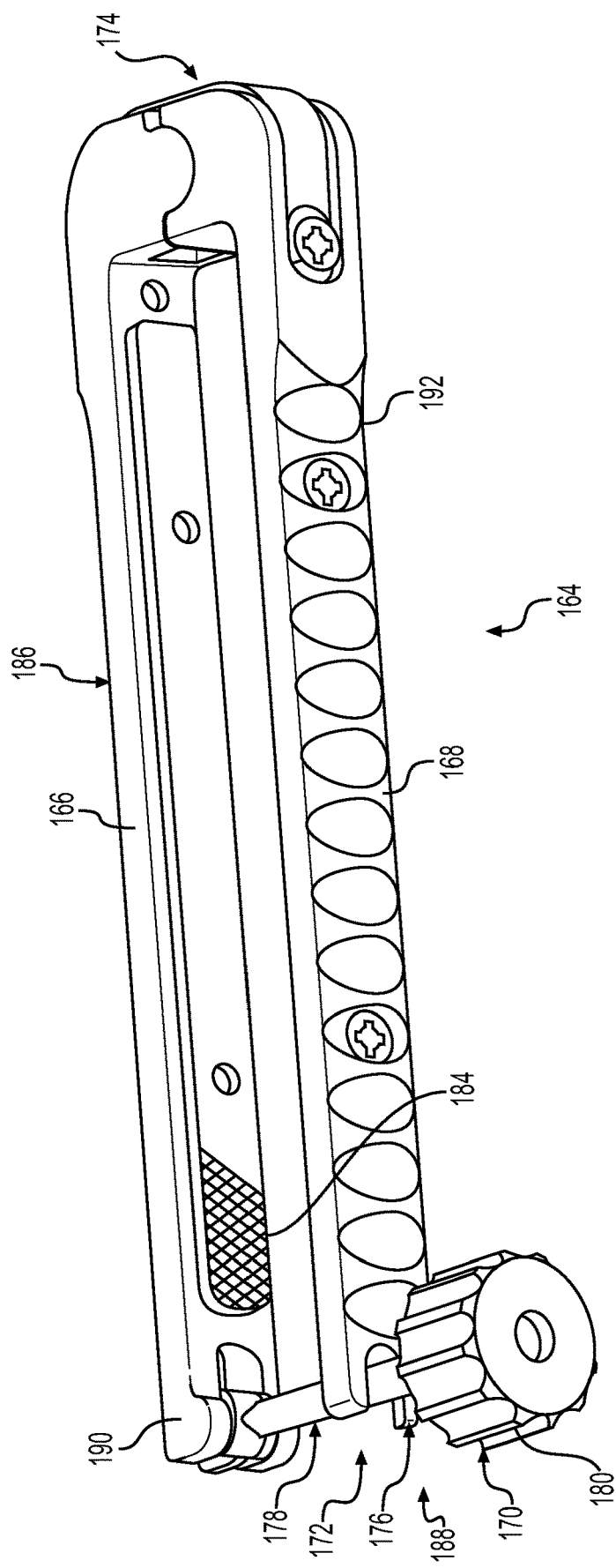
FIG. 10 illustrates a perspective view of an alternative clamp member.

In some embodiments, the head member 182 may be distal to the threaded nut 180, as illustrated in FIG. 6A. In other embodiments, for example, as illustrated in FIG. 1, clamp member 165 may include a threaded nut 181 that is distal to the head member 183. Those skilled in the art may appreciate that, except as otherwise described herein, clamp member 165 may include the same features as clamp member 164. FIG. 10 shows an alternative embodiment of an assembly whereby the threaded nut 180 is positioned on an outer surface of the actuator assembly 170.

In some embodiments, the actuator assembly 170 may be pivotably coupled to the first elongate arm 166, for example, at the second end 188 of the clamp member 164. The actuator assembly 170 may be configured to pivot about a pin 190, and in some embodiments, may be configured to pivot by approximately 90 degrees relative to the first elongate arm 166. The actuator assembly 170 may be configured to pivot between a closed position and an open position. In the closed position, the actuator assembly 170 may be generally perpendicular to the first elongate arm 166, and/or at least a portion of the actuator assembly 170 may be received within the receptacle 176. In some embodiments, in the closed position, the threaded nut 180 may be configured to be received between the first and second elongate arms 166, 168. In other embodiments, for example, as illustrated in FIG. 1, when in the closed position, the threaded nut 181 may be configured to be outside of both the first and second elongate arms 167, 169. In the open position, the actuator assembly 170 may be generally parallel to the first elongate arm 166. In some embodiments, the clamp member 164 may further include a spring member, such as a cantilever or torsion spring, that may be coupled to the first elongate arm 166 and the actuator assembly 170. In use, when the actuator assembly 170 is pulled or urged to the open position and released, the spring member may apply force on the actuator assembly 170 to pivot or return the actuator assembly 170 towards the closed position (e.g., towards the receptacle 176, relative to the first elongate arm 166).

The clamp member 164 may be configured to clamp, couple, engage, and/or secure at least two derotation towers. In use, the clamp member 164 may be pulled open by pivoting the actuator assembly 170 to the open position and pulling, urging, and/or pivoting the first and second arms 166, 168 apart. The clamp member 164 may then be placed around at least two derotation towers (e.g., around two or more proximal derotation tubes). For example, the at least two derotation tubes may be placed between the first and second arms 166, 168. Advantageously, the retaining surfaces on the derotation tubes and/or inner surfaces of the first and second arms 166, 168 may retain or increase friction between the members. The first and second arms 166, 168 may be brought together and the actuator assembly 170 may be pivoted towards the receptacle 176 to the closed position, with at least a portion of the actuator assembly 170 (e.g., the head member 182) inserted into and/or received within the receptacle 176. The derotation towers may be clamped within the clamp member 164 by threading the nut 180 along the rod 178. The head member 182, which may be captured within the receptacle 176 of the second arm 168, may urge the second arm 168 towards the first arm 166 to reduce a distance between the first and second arms 166, 168 at the second end 188 of the clamp member 164. The head member 182 may rest within a countersink of the receptacle 176, thereby inhibiting the second arm 168 from being released.

Figure 6B:
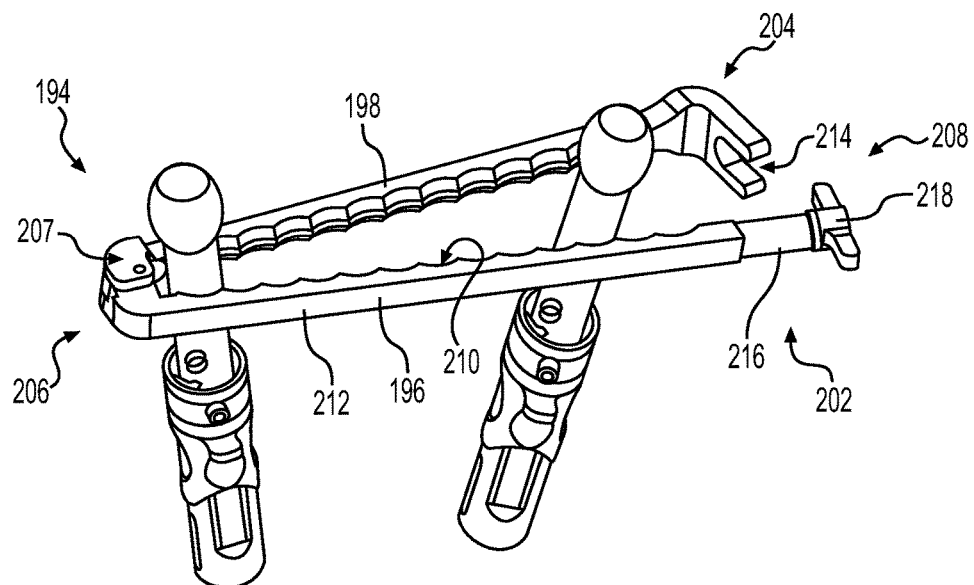
FIGS. 6B-D illustrate perspective views of a clamp member transitioning from an unlocked to a locked configuration as described herein.
Figure 6C:
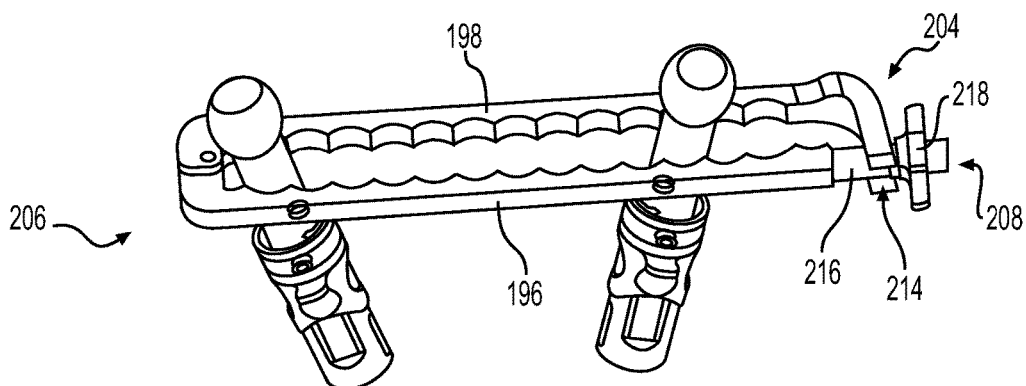
Figure 6D:
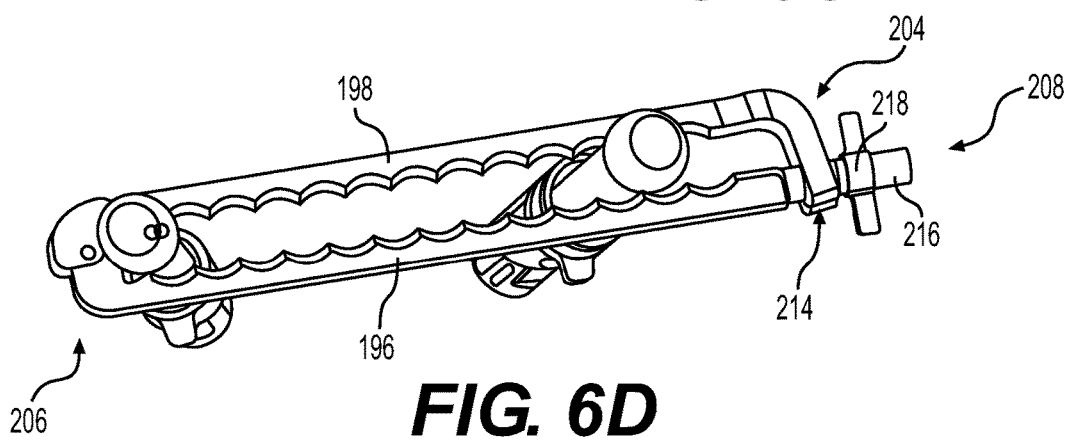

Turning to FIGS. 6B-D, an alternative embodiment of a clamp member is illustrated. Clamp member 194 can include a first elongate arm 196 and a second elongate arm 198. The first elongate arm 196 can be coupled to an actuator assembly 202 and the second elongate arm can include a receiving portion 204 extending therefrom. Clamp member 194 can also include a first end 206 and a second end 208. The first and second arms 196, 198 may be coupled together at the first end 206, for example, by a hinge member 207. Clamp member 194 may include a longitudinal axis that extends between the first and second ends 206, 208.

The first arm 196 can include an inner surface 210 and an outer surface 212, wherein the inner surface 210 is closer to the second arm 198 and the outer surface is farther from the second arm 198. The term "inner surface" can refer to a surface attached to the first arm 196, as well as to the direct surface of the first arm 196. The inner surface 210 can advantageously include a retaining (e.g., friction-increasing) feature. In some embodiments, the inner surface 210 may include a variable surface feature, and may be, for example, angled, non-smooth, abrasive, roughened, increased-friction, coarse, grainy, sandblasted, knurled, texturized, bumpy, ridged, toothed, and/or irregular. In other embodiments, the retaining feature may be soft, compressive, and/or compliant. For example, the retaining feature may be a polymeric (e.g., silicone) surface. In yet other embodiments, the retaining feature can include a scalloped surface, e.g., a plurality of indentations, wherein each indentation is configured to nest a portion of a derotation apparatus therein, as illustrated in FIGS. 6B-D. The second arm 198 can also have an inner surface having some or all of the same features as the inner surface 210. In some embodiments, the outer surface of the first and/or second arms may also include a retaining feature. For example, in some embodiments the outer surface of either or both arms can include a plurality of curved depressions or indentations (not shown).

The first and second elongate arms 196, 198 may be pivotably coupled at the first end 202 of the clamp member 194. The first and second elongate arms 196, 198 may also be coupled to a spring member, such as a cantilever or torsion spring, at the first end 206. Thus, in use, when the arms 196, 198 are pulled apart and subsequently released, the spring member may pull the arms 196, 198 back towards each other.

As illustrated in FIGS. 6B-D, the receiving portion 204 may extend at an oblique angle (e.g., greater than 90 degrees) relative to the second elongate arm 198. In other embodiments, the receiving portion 204 may be perpendicular to the second elongate arm 198. The receiving portion 204 can include a receptacle 214 therein. At least a portion of the actuator assembly 202 may be configured to be reversibly received within the receptacle 214. As illustrated in FIG. 6B, the receptacle 214 can be open on one side and can be, for example, a U-shaped channel or opening. In other embodiments, the receptacle may be a forked opening (e.g., may include two tines defining a channel therebetween). In yet other embodiments, the receptacle can include a tapered opening, e.g., such that the width of the opening of the receptacle is less than the diameter of the receptacle. In some embodiments, the receptacle 214 may have a constant diameter or width as measured longitudinally from the inner surface to the outer surface of the second arm 198. In other embodiments, the receptacle 214 may have a variable diameter or width. For example, the receptacle 214 may be tapered (e.g., conical or frustoconical). In some embodiments, the receptacle 214 can include a countersink configured to nest a portion of the actuator assembly 202 (e.g., nut 218) therein.

The actuator assembly 202 can include a threaded rod 216 and a threaded nut 218. The threaded nut 218 can be generally cylindrical and can include a threaded passageway configured to mate with the threaded rod 216. In some embodiments, the threaded nut 218 can include a gripping surface, such as a plurality of alternating ridges and valleys. As illustrated in FIGS. 6B-D, the threaded nut 218 can include two gripping wings, and may be referred to as a wing nut. In some embodiments, the threaded nut 218 can be coupled to a head member (not shown), as described herein with respect to clamp member 164.

As illustrated in FIGS. 6B-D, the threaded rod 216 may be coupled (e.g., affixed, connected, and/or attached) to the first arm 196. The threaded rod 216 may have an axis that is generally parallel to a length of the first arm 196. The threaded rod 216 may have a length that is greater than a width of the second arm 198. As described herein, the threaded rod 216 may be configured to be reversibly received within the receptacle 214 of the second arm 198.

The clamp member 194 may be configured to clamp, couple, engage, and/or secure at least two derotation towers. In use, the first and second arms 196, 198 may be pulled, urged, and/or pivoted apart and placed around two or more derotation towers (e.g., around two or more proximal derotation tubes), as illustrated in FIG. 6B. For example, the at least two derotation tubes may be placed between the first and second arms 196, 198. Advantageously, the derotation tubes may nest within and/or against the scalloped features on the inner surfaces of the first and second arms 196, 198. The first and second arms 196, 198 may be brought together so that the threaded rod 216 of the first arm 196 is received within the receptacle 214 of the second arm 198, as illustrated in FIG. 6C. The derotation towers may be clamped within the clamp member 194 by threading the nut 218 along the rod 216 towards the first end 206 of the clamp member 194, as illustrated in FIG. 6D. As the nut 218 moves along the rod 216, it may exert pressure on the receiving portion 204. In embodiments where the receiving portion 204 is obliquely angled, applying pressure on the receiving portion 204 may cause the second arm 198 to pivot towards the first arm 196, thereby clamping the derotation towers therebetween and/or reducing a distance between the first and second arms 196, 198 at the second end 208 of the clamp member 194. The threaded nut 218 may nest within a countersink of the receptacle 214, thereby inhibiting the second arm 198 from being released.

Figure 7:
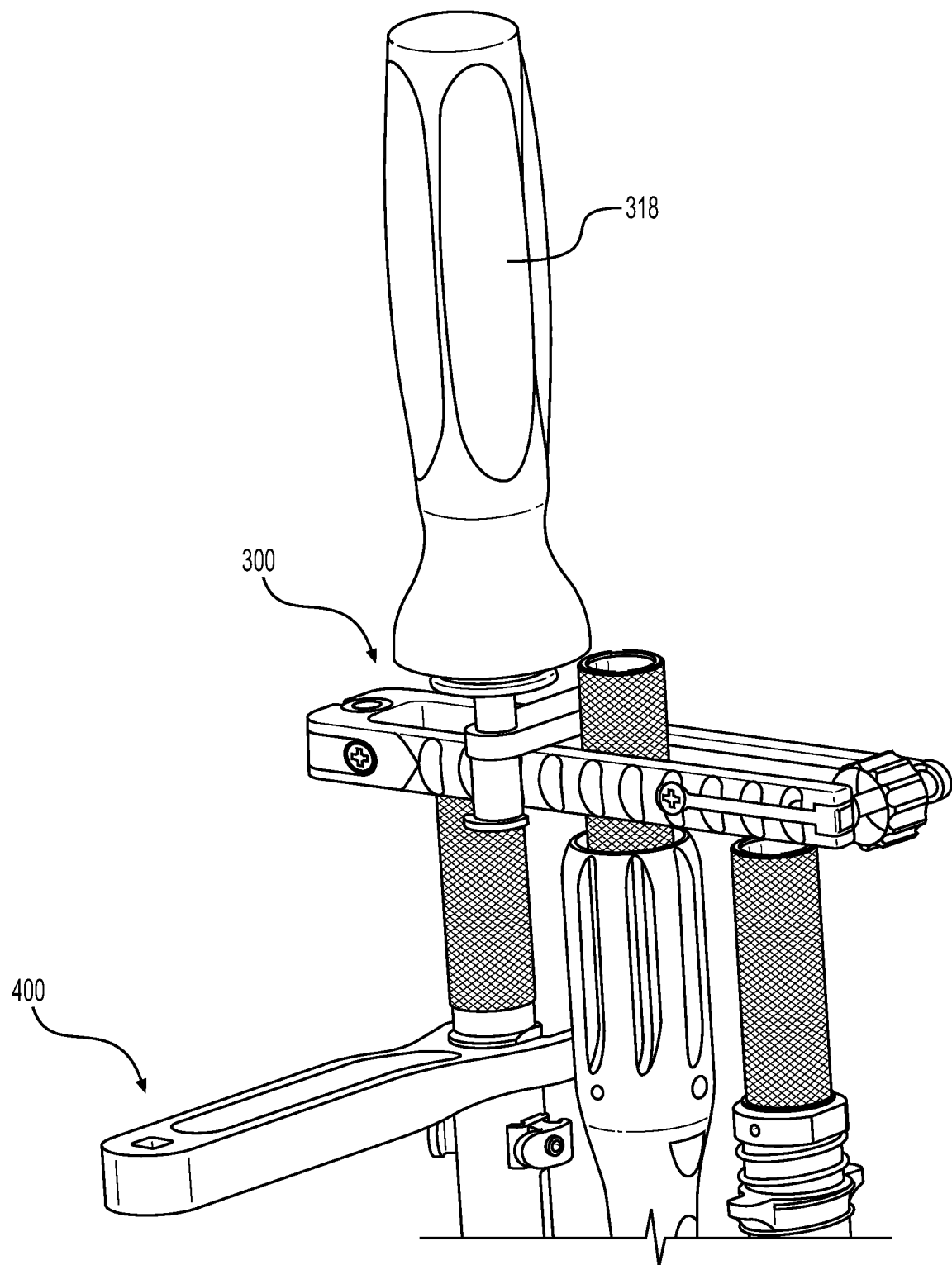
FIG. 7 illustrates a perspective view of a handle assembly coupled to a clamp member and a countertorque device coupled to a derotation tower as described herein.
Figure 8:
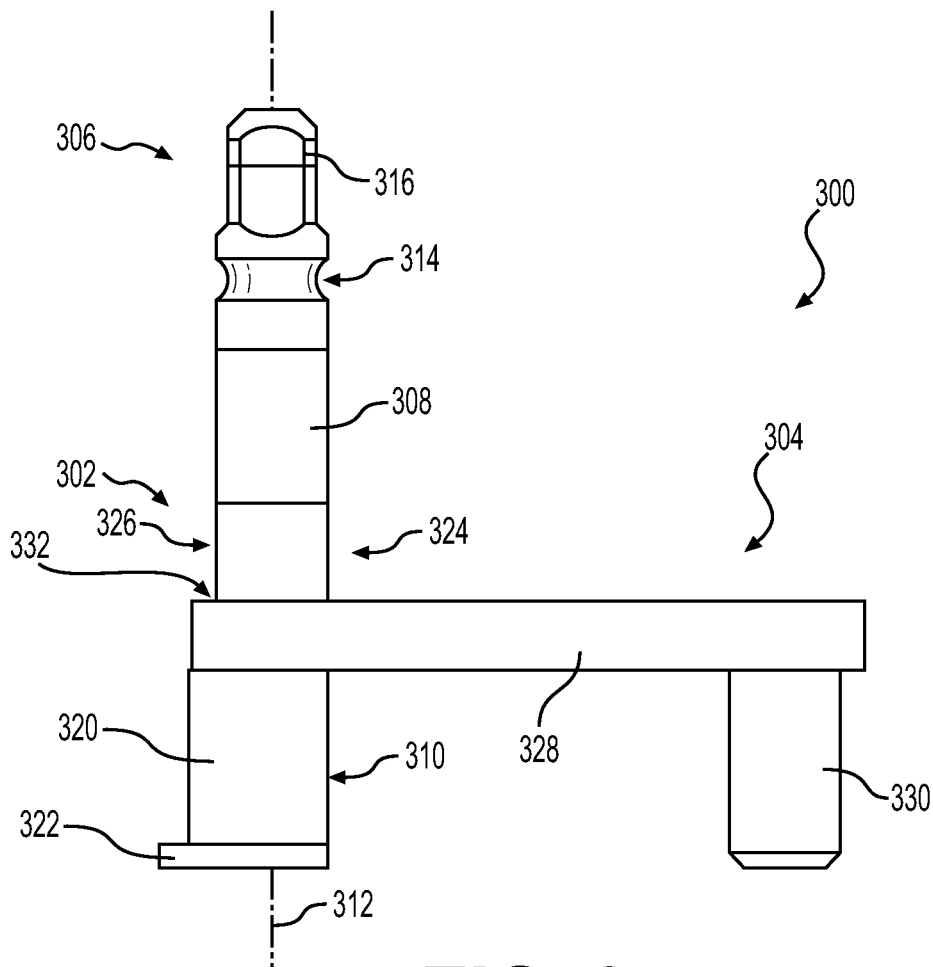
FIG. 8 illustrates a handle assembly as described herein.

Derotation systems described herein may also include a handle assembly 300, as illustrated in FIGS. 7-8. The handle assembly 300 may be configured to engage or couple with any of the clamp members disclosed herein (e.g., clamp member 164, clamp member 165, and/or clamp member 194). In some embodiments, the handle assembly 300 may be configured to engage or couple with a single clamp member. In use, the handle assembly 300 may be configured to transmit force to the spine through the derotation system as part of a derotation procedure. As illustrated in FIG. 8, the handle assembly 300 can include an elongate member 302 and a plate member 304. The elongate member 302 may be rotatably coupled to (e.g., may be configured to rotate within) the plate member 304. The elongate member can include a proximal handle-engaging portion 306, a first leg 310, and a cylindrical body 308 therebetween. The elongate member 302 may be configured to rotate about longitudinal axis 312. The handle-engaging portion 306 can include a circumferential, rounded groove 314 and/or an angled proximal head 316. As illustrated in FIG. 8, the angled proximal head 316 can include four beveled walls and can include, for example, a generally square or rectangular transverse cross-section. The handle-engaging portion 306 can be configured to couple with a handle 318, as illustrated in FIG. 7. In use, the handle 318 can be grasped by a user to apply force to the derotation system.

As illustrated in FIG. 8, the first leg can include an eccentrically-shaped member 320 and/or a distal lip 322 extending therefrom. The eccentrically-shaped member 320 may have a length, as measured along the longitudinal axis 312, which is greater than or equal to a height of a clamp member. The eccentrically-shaped member 320 may have a transverse area that is greater than that of the cylindrical body 308 of the elongate member 302. When viewed along the longitudinal axis 312, the eccentrically-shaped member 320 may have an area that is not equally distributed around the longitudinal axis 312. In some embodiments, the eccentrically-shaped member 320 may have a non-circular and/or non-symmetrical transverse cross-section. For example, the eccentrically-shaped member 320 may be elliptical, ovular, and/or egg-shaped. The eccentrically-shaped member 320 may be referred to herein as a cam member. The distal lip 322 may have a transverse area that is greater than that of the cylindrical body 308 and/or the eccentrically-shaped member 320. When viewed along the longitudinal axis 312, the distal lip 322 may have an area that is not equally distributed around the longitudinal axis 312. Both the eccentrically-shaped member 320 and the distal lip 322 may extend radially beyond the cylindrical body 308 at some points along a circumference of the cylindrical body 308. As illustrated in FIG. 8, the elongate member 302 may generally include a first, unlocked section or portion 324 where the cylindrical body 308, eccentrically-shaped member 320, and lip 322 are aligned (e.g., flush), and a second, unlocked section or portion 326 where the cylindrical body 308, eccentrically-shaped member 320, and lip 322 are staggered (e.g., the eccentrically-shaped member 320 and the lip 322 may each extend radially outward relative to the cylindrical body 308). The elongate member 302 may be configured to rotate between a locked and unlocked configuration. In the unlocked configuration, illustrated in FIG. 8, the unlocked portion of the elongate member 302 may be facing inwards (e.g., towards the second leg 330, described herein) and the locked portion may be facing outwards (e.g., away from the second leg 330). In the locked configuration, the unlocked portion of the elongate member 302 may be facing outwards and the locked portion may be facing inwards.

As illustrated in FIG. 8, the plate member 304 can include a body 328 and a second leg 330. The handle assembly 300 may be configured to receive a clamp member between the first and second legs 310, 330. The body 328 of the plate member 304 may be generally flat and/or planar. The body 328 may include a receptacle 332 configured to receive the elongate member 302 therethrough. The second leg 330 may extend perpendicularly or orthogonally from the plate member 304. In some embodiments, the second leg 330 may be affixed or attached to the body 328. In other embodiments, the plate member 304 may be a unitary structure. The second leg 330 may be cylindrical.

In use, a clamp member may be positioned between the first and second legs 310, 330 when the handle assembly 300 is in the unlocked configuration (e.g., the unlocked portion of the elongate member 302 is facing inwards). To couple the handle assembly 300 to the clamp member, the elongate member 302 may be rotated to the locked configuration. The portion of the eccentrically-shaped member 320 that extends radially beyond the cylindrical body 308 may rotate into engagement with the clamp member to secure it in a friction fit between the first and second legs 310, 330. Additionally, the portion of the lip 322 that extends radially beyond the cylindrical body 308 may rotate to a position below the clamp member, further securing the engagement between the clamp member and the handle assembly 300.

Figure 9:
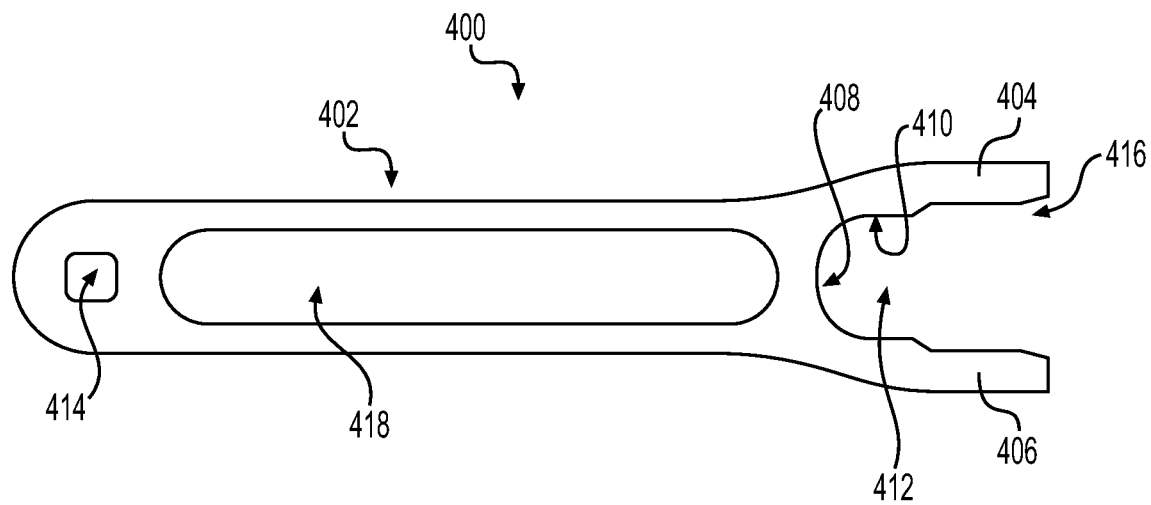
FIG. 9 illustrates a countertorque device as described herein.

Derotation systems described herein may also include a countertorque device 400, as illustrated in FIGS. 7 and 9. The countertorque device 400 may be generally flat and/or planar. As illustrated in FIG. 9, the countertorque device 400 can include an elongate body 402 having first and second prongs 404, 406 extending distally therefrom. The first and second prongs 404, 406 can define a channel or cavity 412 therebetween. The cavity 412 can include a curved section 408 and a linear, straight, and/or flat section 410. As illustrated in FIG. 9, the linear section 410 may be distal to the curved section 408. The cavity 412 can also include a mouth or opening 416 that may be wider than the curved and/or linear sections 408, 410, as measured between the first and second prongs 404, 406. A proximal section of the elongate body 402 may include an angular hole 414 passing from a top surface to a bottom surface thereof. As illustrated in FIG. 9, the angular hole 414 may have four walls and can be generally square or rectangular. In other embodiments, the angular hole may have a different number of walls, such as 3, 4, 5, 6, 7, or 8, and may be, for example, triangular, rectangular, pentagonal, hexagonal, heptagonal, or octagonal. The angular hole 414 may be configured to receive and engage the angular head 316 of the handle assembly 300. In some embodiments, the elongate body 402 may be generally hollow. For example, as illustrated in FIG. 9, the elongate body 402 may include an elongate hole 418 passing from the top surface to the bottom surface thereof.

In use, a derotation tower may be positioned between first and second prongs 404, 406 and within in the cavity 412, as illustrated in FIG. 7. The flat section 410 of the cavity may align with flat section(s) on the derotation towers. The countertorque device 400 may be grasped by a user to prevent a moment from being transferred to an overall construct and/or patient Some embodiments herein are directed to methods of installing the derotation towers and systems described herein. These methods can include providing a plurality of anchor members and derotation towers and/or engaging one or more derotation towers with one or more anchor members as described herein. In some embodiments, each derotation tower can be engaged with a separate and/or different anchor member (e.g., each anchor member may be engaged with only one derotation tower). Each derotation tower can include a proximal derotation tube (e.g., proximal derotation tube 6 or 16) coupled to a distal engagement assembly (e.g., distal engagement assembly 8, 20, or 44, or rod reducer assembly 80, 118, or 140). As described herein, the anchor member can include an anchor or fastener, such as a pedicle screw or hook, and a housing, such as a tulip head. The anchor or fastener may be at least partially received within the housing. The anchor member may include an elongate rod associated therewith. For example, the elongate rod may be disposed within a channel on the housing. Each derotation tower may be engaged with a separate anchor member. In some embodiments, a plurality of derotation towers may be engaged with a plurality of anchor members.

In some embodiments, one or more derotation towers can include a distal engagement assembly, such as distal engagement assembly 20 or 44, as illustrated in FIGS. 4A-C. As described herein, these assemblies may include an outer sleeve (e.g., outer sleeve 22 or 46) slideably disposed over an inner sleeve (e.g., inner sleeve 24 or 48). As described herein, in these embodiments, the step of engaging the derotation tower with the anchor member can include positioning the inner sleeve around at least a portion of the anchor member (e.g., the housing) and translating the outer sleeve distally.

In some embodiments, one or more derotation towers can include a distal engagement assembly that includes a rod reducer assembly, such as rod reducer assembly 80, 118, or 140, as illustrated in FIGS. 5A-D. In these embodiments, the derotation tower may be configured to urge an elongate rod into engagement with an anchor member. For example, in embodiments where the anchor member includes a housing having a rod-receiving channel, the derotation tower may be configured to urge the elongate rod distally into the channel. In these embodiments, the step of engaging a plurality of derotation towers with a plurality of anchor members may include pushing or urging at least one elongate rod into engagement with the anchor members.

In some embodiments, the derotation tower may include a distal engagement assembly that includes a rod reducer assembly 80, illustrated in FIGS. 5A-B. As described herein, in these embodiments, the rod reducer assembly 80 may include a connector member 82, a clip reducer 84 reversibly coupled with the connector member 82 and comprising a reduction member 102 and a distal end 98, and a threaded driver. The step of engaging the derotation tower with an anchor member (e.g., anchor member 28) can include positioning the distal end 98 around at least a portion of the anchor member (e.g., the housing) and threading the threaded driver through the clip reducer 84 to actuate the reduction member 102.

In some embodiments, the derotation tower may include a distal engagement assembly that includes rod reducer assembly 118, illustrated in FIG. 5C. As described herein, in these embodiments, the rod reducer assembly 118 may include a clip reducer 120 and a threaded driver 122. The clip reducer 120 can include a reduction member 134 and a distal end 126. The step of engaging the derotation tower with an anchor member can include positioning the distal end 126 around at least a portion of the anchor member (e.g., the housing) and threading the threaded driver 122 through the clip reducer 120 to actuate the reduction member 134.

In some embodiments, the derotation tower may include a distal engagement assembly that include rod reducer assembly 140, illustrated in FIG. 5D. As described herein, in these embodiments, the rod reducer assembly 140 may include an inner sleeve 142, an outer sleeve 144 slideably disposed over the inner sleeve 142, and a rotatable handle 146 configured to actuate the outer sleeve 144. The step of engaging the derotation tower with an anchor member (e.g., anchor member 28) can include positioning the distal end 150 around at least a portion of the anchor member (e.g., the housing) and rotating the rotatable handle 146 to actuate the outer sleeve 144.

Methods of installing the derotation systems described herein may also include placing, clamping, and/or securing a first clamp member around a first group of at least two derotation tubes (e.g., first and second derotation tubes) of at least two derotation towers (e.g., first and second derotation towers) along a first axis, to thereby couple together the derotation tubes. In some embodiments, the first axis may be a longitudinal axis or a latitudinal axis. In other embodiments, the first axis may be a medial-lateral or cephalad-caudal (e.g., superior-inferior) axis. Any combinations of the clamp members described herein, e.g., clamp member 164, 165, and/or 194, can be used as the first clamp member in the derotation systems of the present disclosure. As described herein, the first clamp member may include a first elongate arm coupled to an actuator assembly and a second elongate arm having a receiving portion extending therefrom, wherein the actuator assembly includes a threaded rod and a threaded nut. The step of clamping the first clamp member around the first group of at least two derotation tubes can include opening the first clamp member by pivoting apart the first and second elongate arms, placing the first group of at least two derotation tubes between the first and second elongate arms, inserting at least a portion of the actuator assembly of the first arm into a receptacle in the receiving portion of the second arm, and threading the nut on the rod to reduce a distance between the first and second elongate arms at a second end of the first clamp member.

Methods of installing the derotation systems described herein may also include placing, clamping, and/or securing a second clamp member around a second group of at least two derotation tubes (e.g., first and third derotation tubes) of at least two derotation towers (e.g., first and third derotation towers) along a second axis, to thereby couple together the derotation tubes. Any combinations of the clamp members described herein, e.g., clamp member 164, 165, and/or 194, can be used as the second clamp member in the derotation systems of the present disclosure. The second clamp member can be placed, clamped, and/or secured around the second group of derotation tubes according to the method described herein of placing, clamping, and/or securing the first clamp member around the first group of derotation tubes. As illustrated in FIG. 1, a second clamp member may be positioned on a derotation tower distal to a first clamp member, or vice versa.

In some embodiments, the second axis may be a longitudinal axis or a latitudinal axis. In other embodiments, the second axis may be a medial-lateral or cephalad-caudal (e.g., superior-inferior) axis. Advantageously, the second axis may be skewed relative to the first axis (e.g., the first and second axes would intersect if in the same plane). For example, the first axis can be a longitudinal axis and the second axis can be a latitudinal axis, or vice versa. In another example, the first axis can be a medial-lateral axis and the second axis can be a cephalad-caudal axis, or vice versa. In some embodiments, if in the same plane, the first and second axes would be perpendicular and/or orthogonal.

In some embodiments, one derotation tube (e.g., a single derotation tower), such as the first derotation tube, may be a member of both the first and second groups of derotation tubes. Thus, the first and second clamp members may overlap on the one derotation tube. Additionally, the one derotation tube may link the first and second groups together to assemble a derotation system, which may be referred to herein as a unified (e.g., interconnected) derotation system construct. In some embodiments, at least two or more derotation tubes (e.g., derotation towers) in the system can be coupled or clamped to at least two other derotation towers using at least two different clamp members. In some embodiments, each derotation tower in the system can be coupled or clamped to at least two other derotation towers along two different, skewed axes and using at least two different clamp members.

Some embodiments can include clamping each derotation tower to at least two other derotation towers along first and second axes, respectively, for example, as illustrated in FIG. 1. For example, in a system including at least first, second, and third derotation towers, the first derotation tower can be coupled or clamped to the second derotation tower along the first axis, and can be coupled or clamped to the third derotation tower along the second axis. The first and second axes may be skewed relative to each other. In these embodiments, the step of clamping each derotation tower to at least two other derotation towers can include clamping at least two (e.g., first and second) clamp members around each derotation tower. The first clamp member may extend along the first axis and the second clamp member may extend along the second axis. In some embodiments, each derotation tower can be clamped to an adjacent ipsilateral derotation tower and an adjacent contralateral derotation tower. Thus, those skilled in the art may appreciate that the derotation systems of the present disclosure can include any number of derotation towers and/or clamp members. As illustrated in FIG. 1, for example, in some embodiments the derotation system can include eight derotation towers and six clamp members.

In use, the derotation towers may be engaged with a plurality of anchor members along two sides of a patient's spine. Advantageously, each derotation tower may be clamped to at least one derotation tower on the same side of the spine (e.g., ipsilaterally) and at least one on the opposite side of the spine (e.g., contralaterally). In some embodiments, each derotation tower may be coupled or clamped to at least two other derotation towers along two different, skewed axes. Advantageously, this can provide the derotation system with stability, as compared to a system that may only allow coupling of some towers, for example, on a single side of the spine, and can thereby enable a user to effectively apply controlled force during a derotation procedure.

Those skilled in the art may appreciate that the derotation towers and/or systems described herein may be used to treat a spinal irregularity, such as an irregular curvature (e.g., scoliosis), for example, in a derotation procedure. In a derotation procedure, a derotation system may be installed as described herein along a patient's spine adjacent to the spinal irregularity. As described herein, the system may include a plurality of derotation towers installed along both sides of the patient's spine and coupled together via clamp members either ipsilaterally and/or contralaterally. In some embodiments, the system can include a plurality of derotation towers coupled together with clamp members in both medial-lateral and cephalad-caudal directions.

Methods described herein can optionally include coupling a handle assembly (e.g., handle assembly 300) to one of the first and second clamp members (e.g., clamp member 164, 165, or 194). As described herein, handle assembly 300 can include an elongate member 302 rotatably coupled to a plate member 304, wherein the elongate member 302 can include a first leg 310 that can include an eccentrically-shaped member 320 and/or a distal lip 322. This step can include positioning the clamp member widthwise between the first and second legs 310, 330 of the handle assembly 300. For example, the first arm of the clamp member may be adjacent the first leg of the handle assembly and the second arm may be adjacent the second leg, or vice versa. In some embodiments, the clamp member, for example, as illustrated in FIG. 6A with respect to clamp member 164, can include a plurality of curved depressions or indentations 192. In these embodiments, the first and second legs 310, 330 of the handle assembly 300 may nest within these depressions or indentations 192. Advantageously, this feature may encourage a secure engagement between these components. The step of coupling the handle assembly to the clamp member can also include locking and/or securing the handle assembly to the clamp member. This step can include rotating the first leg, for example, from an unlocked configuration to a locked configuration as described herein, to thereby engage the eccentrically-shaped member 320 with the clamp member. In embodiments that include distal lip 322, the step of rotating the first leg 310 can also include rotating the distal lip 322 towards the second leg 330 and/or towards (e.g., under) the clamp member. The clamp member may thereby be retained, held, and/or positioned between the body 328 and the distal lip 322 of the handle assembly 300.

In some embodiments, a handle (e.g., handle 318) can be coupled to the handle assembly 300. In some embodiments, this step may be performed prior to coupling the handle assembly 300 to one of the clamp members. For example, this step may be performed prior to locking the handle assembly 300, e.g., prior to rotating the first leg 310 from the unlocked configuration to the locked configuration. In these embodiments, the step of coupling the handle assembly 300 with the handle 318 can include inserting at least a portion of the proximal handle-engaging portion 306 into a socket in the handle. The handle 318 can be grasped by a user to apply force to the handle assembly 300. Thus, the step of rotating the first leg 310 can include rotating or turning the handle 318 to apply torque to the first leg 310. In some embodiments, the handle assembly 300 and the handle 318 can be connected or coupled via a quick-connect coupling. In other embodiments, the handle 318 can include a compressible member configured to be retained within the circumferential groove 314 on the proximal handle-engaging portion 306.

Methods herein can also include applying force to the handle assembly 300, e.g., by applying force to the handle 316, to adjust a position (e.g., angle and/or orientation) of at least one derotation tower. As the derotation tower may be coupled to an anchor member, this step can also include adjusting a position of the anchor member. Advantageously, because multiple (e.g., all) derotation towers may be coupled together in the derotation system, force applied to the handle assembly 300 may be distributed throughout the entire system to adjust a position thereof. In embodiments where each derotation tower is coupled to at least two different towers in two different directions, the derotation system may advantageously configured to sturdily receive and distribute force evenly therethrough. In a spinal derotation procedure, a user may apply force to the handle to adjust and/or correct the curvature and/or rotation of a patient's spine.

Some methods may also include coupling and/or securing the anchor member (e.g., a pedicle screw and/or housing) with a fastener (e.g., a set screw or locking cap). In these embodiments, the fastener may be passed longitudinally and/or axially through the derotation tower to the anchor member. A countertorque device (e.g., countertorque device 400) may be engaged with the derotation tower. For example, this may include positioning the derotation tower within the cavity 412 (e.g., between the first and second prongs 404, 406) of the countertorque device 400. In embodiments where the derotation tower includes one or more flat exterior sections as described herein, this step can include aligning the flat exterior sections with the linear or straight section 410 of the cavity 412. In embodiments where the derotation tower includes a flattened section having two parallel walls, this step can include aligning the two parallel walls with the linear or straight section 410 of the cavity 412.

Subsequently, an elongate driver may be passed longitudinally and/or axially through the derotation tower to engage the fastener. Force may be applied to the driver while the countertorque device 400 is engaged with the derotation tower to couple the fastener member to the anchor member (e.g., to thread a set screw into a housing or tulip head). In some embodiments, an elongate rod may be associated with the anchor member. For example, an elongate rod may be disposed within a channel on a housing of the anchor member. In these embodiments, applying force to the driver, while the countertorque device 400 is engaged with the derotation tower, may also result in securing the anchor member to the elongate rod and/or securing an angle of the anchor member relative to the elongate rod. Those skilled in the art may appreciate that the countertorque device may advantageously allow the driver and fastener to rotate while preventing or inhibiting the derotation tower and/or anchor member from rotating.

Some methods may also include disengaging the handle assembly 300 from the clamp member. This step can include placing the angled proximal head 316 of the handle assembly 300 into the angular hole 414 of the countertorque device 400 and applying force to the countertorque device to unlock the handle assembly 300 by rotating the eccentrically-shaped member 320 and/or distal lip 322 out of engagement with the clamp member (e.g., to rotate the eccentrically-shaped member 320 from the locked configuration to the unlocked configuration).

Some embodiments herein are directed to a kit that can include any combination of the devices and components described herein. For example, some embodiments can include a plurality of derotation towers, a plurality of clamp members, a plurality of handle assemblies, and/or a plurality of countertorque devices. Multiple variants of derotation towers, clamp members, handle assemblies, and/or countertorque devices can also be included in a single kit. Furthermore, the kit can include a variety of different sizes of each device. The kit can additionally include one or more other devices, tools, and/or materials configured for use in conjunction with the derotation system or its components. For example, a kit may include one or more handles, fasteners (e.g., pedicle screws or hooks), housings (e.g., tulip heads), elongate rods, set screws, locking caps and/or drivers. In some embodiments, for example, where the kit does not include a derotation tower configured for rod reduction, the kit may additionally include a rod reducer. In other embodiments, the kit can include one or more additional instruments configured for use during the installation procedure, such as a probe, forceps, inserter, retractor, distractor, compressor, and/or rod bender. In yet other embodiments, the kit can include one or more additional implants, such as an intervertebral cage, plate, transverse rod connector, and/or bone graft material. In yet other embodiments, the systems described above can be used with various fusion devices (spacers, plates, rods) and prosthetic devices.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A derotation system, comprising:
   first and second derotation towers, wherein each derotation tower comprises a proximal derotation tube coupled to a distal engagement assembly that is configured to engage an anchor member;
   a clamp member, having a first elongate arm and a second elongate arm, configured to receive the first and second derotation towers, the clamp member having an inner surface including an engagement feature, and the engagement feature is configured to engage an outer surface of the first or second derotation tower; and
   a handle assembly configured to engage the clamp member,
   wherein the distal engagement assembly includes a first rod reducer assembly and a second rod reducer assembly,
   wherein each rod reducer assembly includes an inner sleeve, an outer sleeve slideably disposed over the inner sleeve, and a rotatable handle configured to actuate the outer sleeve,
   wherein the engagement feature is a series of at least three non-deformable plurality of curved depressions along each of the first elongate arm and the second elongate arm, and each of the plurality of curved depressions is configured to engage an outer surface of the first or second derotation tower,
   wherein the first elongate arm and the second elongate arm are coupled at a first end via a hinge and the first elongate arm has a threaded rod and nut on a second end, the threaded rod disposed to remain in parallel with a longitudinal axis of the first elongate arm, and
   wherein the second elongate arm has an obliquely angled receiving portion at the second end configured to receive the threaded rod, and
   wherein when the threaded rod is received in the receiving portion and the nut is actuated, the second elongate arm pivots toward the first elongate arm due to the obliquely angled receiving portion to clamp the first and second derotation towers.

2. The system of claim 1, wherein each derotation tube comprises a longitudinal axis and a variable transverse outer surface thereabout.

3. The system of claim 2, wherein the variable transverse outer surface comprises a plurality of angled surfaces.

4. The system of claim 2, wherein at least one derotation tube comprises first and second rotatable members in series along the longitudinal axis.

5. The system of claim 2, wherein the variable transverse outer surface comprises a knurled surface.

6. The system of claim 1, wherein the outer sleeve comprises at least two concave gripping surfaces.

7. The system of claim 1, wherein each rod reducer assembly is configured to reduce a rod engaged with the anchor member.

8. The system of claim 7, wherein each rod reducer assembly comprises:
   a connector member;
   a clip reducer configured to be reversibly coupled with the connector member and comprising a reduction member and a distal end configured to engage the anchor member; and
   a threaded driver configured to actuate the reduction member.

9. The system of claim 7, wherein each rod reducer assembly comprises:
   a clip reducer comprising a translatable reduction member and a distal end configured to engage the anchor member; and
   a threaded driver configured to actuate the reduction member.

10. A derotation system, comprising:
    a plurality of derotation towers, wherein each derotation tower comprises a derotation tube;
    a plurality of clamp members each having a first elongate arm, a second elongate arm, and a longitudinal axis, wherein each clamp member is configured to engage at least two derotation tubes, the clamp member having an inner surface including an engagement feature, and the engagement feature is configured to engage an outer surface of the plurality of derotation towers; and
    a handle assembly configured to engage one of the clamp members,
    wherein the engagement feature is a series of at least three non-deformable plurality of curved depressions along each of the first elongate arm and the second elongate arm, and each of the plurality of curved depressions is configured to engage an outer surface of the first or second derotation tower,
    wherein the first elongate arm and the second elongate arm are coupled at a first end via a hinge and the first elongate arm has a threaded rod and nut on a second end, the threaded rod disposed to remain in parallel with a longitudinal axis of the first elongate arm, and wherein the second elongate arm has an obliquely angled receiving portion at the second end configured to receive the threaded rod, and wherein when the threaded rod is received in the receiving portion and the nut is actuated, the second elongate arm pivots toward the first elongate arm due to the obliquely angled receiving portion to clamp the derotation towers.

11. The system of claim 10, wherein the handle assembly comprises an elongate member rotatably coupled to a plate member, wherein:

the elongate member comprises a proximal handle-engaging portion, a first leg, and a cylindrical body therebetween; and the plate member comprises a body and a second leg extending orthogonally therefrom;

wherein the handle assembly is configured to receive one of the clamp members between the first and second legs.

12. The system of claim 10, further comprising a countertorque device comprising an elongate body having first and second prongs extending distally therefrom and defining a cavity therebetween, wherein the cavity comprises a curved section and a linear section.

13. A derotation kit, comprising:

a plurality of derotation towers, wherein each derotation tower comprises a proximal derotation tube;

at least one clamp member, having a first elongate arm and a second elongate arm, wherein the clamp member is configured to engage at least two derotation towers, the at least one clamp member having an inner surface including an engagement feature, and the engagement feature is configured to engage an outer surface of the plurality of derotation towers;

at least one handle assembly, wherein the handle assembly is configured to engage at least one clamp member; and at least one countertorque device, wherein the countertorque device is configured to engage at least one derotation tower, wherein the engagement feature is a series of at least three non-deformable plurality of curved depressions along each of the first elongate arm and the second elongate arm, and each of the plurality of curved depressions is configured to engage an outer surface of the first or second derotation tower, wherein the first elongate arm and the second elongate arm are coupled at a first end via a hinge and the first elongate arm has a threaded rod and nut on a second end, the threaded rod disposed to remain in parallel with a longitudinal axis of the first elongate arm, and wherein the second elongate arm has an obliquely angled receiving portion at the second end configured to receive the threaded rod, and wherein when the threaded rod is received in the receiving portion and the nut is actuated, the second elongate arm pivots toward the first elongate arm due to the obliquely angled receiving portion to clamp the derotation towers.

\* \* \* \* \*